(12) United States Patent
Nyce

(10) Patent No.: US 7,456,161 B2
(45) Date of Patent: *Nov. 25, 2008

(54) USE OF DHEA AND DHEA-SULFATE FOR THE TREATMENT OF CHRONIC OBSTRUCTIVE PULMONARY DISEASE

(75) Inventor: Jonathan W. Nyce, Titusville, NJ (US)

(73) Assignee: Epigenesis Pharmaceuticals, LLC, Cranbury, NJ (US)

( * ) Notice: Subject to any disclaimer, the term of this patent is extended or adjusted under 35 U.S.C. 154(b) by 738 days.

This patent is subject to a terminal disclaimer.

(21) Appl. No.: 10/454,061

(22) Filed: Jun. 3, 2003

(65) Prior Publication Data

US 2004/0082522 A1  Apr. 29, 2004

Related U.S. Application Data

(63) Continuation-in-part of application No. PCT/US02/12555, filed on Apr. 22, 2002.

(60) Provisional application No. 60/286,124, filed on Apr. 24, 2001.

(51) Int. Cl.
*A61K 31/56* (2006.01)
(52) U.S. Cl. .................. 514/178; 514/180; 514/181; 514/182
(58) Field of Classification Search .................. 514/178, 514/180, 181, 182
See application file for complete search history.

(56) References Cited

U.S. PATENT DOCUMENTS

| | | |
|---|---|---|
| 4,393,066 A | 7/1983 | Garrett et al. |
| 4,499,064 A | 2/1985 | Shive |
| 4,501,729 A | 2/1985 | Boucher et al. |
| 4,575,498 A | 3/1986 | Holmes et al. |
| 4,628,052 A | 12/1986 | Peat |
| 4,920,115 A | 4/1990 | Nestler et al. |
| 4,931,441 A | 6/1990 | Lawrence |
| 4,985,443 A | 1/1991 | Montes |
| 5,021,417 A | 6/1991 | Prost |
| 5,059,595 A | 10/1991 | Le Grazie |
| 5,077,284 A | 12/1991 | Loria et al. |
| 5,110,810 A | 5/1992 | Eich et al. |
| 5,118,505 A | 6/1992 | Költringer |
| 5,162,198 A | 11/1992 | Eich et al. |

(Continued)

FOREIGN PATENT DOCUMENTS

JP  57-128624  8/1982

(Continued)

OTHER PUBLICATIONS

Merck Manual, 16th ed., 1992, p. 658-666.*

(Continued)

*Primary Examiner*—San-ming Hui
(74) *Attorney, Agent, or Firm*—Albert P. Halluin; Robert H. Reamey; Wilson Sonsini Goodrich & Rosati

(57) ABSTRACT

A method for treating or preventing chronic obstructive pulmonary disease (COPD) by using as active agent a non-glucorticoid steroid, analogue thereof, such as dehydroepiandrosterone (DHEA) and dehydroepiandrosterone sulfate (DHEA-S), or their salts, in an amount effective for preventing or treating COPD.

24 Claims, 8 Drawing Sheets

DURATION OF DHEA TREATMENT (h)

U.S. PATENT DOCUMENTS

| | | | |
|---|---|---|---|
| 5,173,488 | A | 12/1992 | Haeger |
| 5,177,076 | A | 1/1993 | Nijkerk et al. |
| 5,266,312 | A | 11/1993 | Leung et al. |
| 5,270,305 | A | 12/1993 | Palmer |
| 5,347,005 | A | 9/1994 | Mueller et al. |
| 5,407,684 | A | 4/1995 | Loria et al. |
| 5,407,927 | A | 4/1995 | Morales et al. |
| 5,489,581 | A | 2/1996 | Daynes et al. |
| 5,527,789 | A | 6/1996 | Nyce |
| 5,532,230 | A | 7/1996 | Daynes et al. |
| 5,538,734 | A | 7/1996 | Le Grazie |
| 5,583,126 | A | 12/1996 | Daynes et al. |
| 5,635,496 | A | 6/1997 | Daynes et al. |
| 5,660,835 | A * | 8/1997 | Nyce ............................ 424/400 |
| 5,686,438 | A | 11/1997 | Daynes et al. |
| 5,703,063 | A | 12/1997 | Chasalow et al. |
| 5,767,278 | A | 6/1998 | Gaeta et al. |
| 5,811,418 | A | 9/1998 | Daynes et al. |
| 5,859,000 | A | 1/1999 | Dowell et al. |
| 5,948,434 | A | 9/1999 | Labrie |
| 6,087,351 | A * | 7/2000 | Nyce ............................ 514/178 |
| 6,093,706 | A | 7/2000 | Zeligs |
| 6,670,349 | B1 * | 12/2003 | Nyce ............................ 514/178 |
| 2002/0042401 | A1 | 4/2002 | Ferguson et al. |
| 2003/0013772 | A1 | 1/2003 | Murphy et al. |
| 2003/0138434 | A1 | 7/2003 | Campbell et al. |
| 2003/0139331 | A1 | 7/2003 | Martin et al. |

FOREIGN PATENT DOCUMENTS

| | | |
|---|---|---|
| JP | 52-99221 | 9/1984 |
| WO | WO 93/16704 | 9/1993 |
| WO | WO 96/16680 | 6/1996 |
| WO | WO 97/48367 | 12/1997 |
| WO | WO 98/03180 | 1/1998 |
| WO | WO 00/54763 | 9/2000 |
| WO | WO 01/15745 | 3/2001 |
| WO | WO 02/069955 | 9/2002 |
| WO | WO 03/072572 | 9/2003 |

OTHER PUBLICATIONS

Araneo et al., "Dehydroepiandrosterone Reduces Progressive Dermal Ischemia Caused by Thermal Injury", *J. Surg. Res.* 59(2):250-62 (1995).

Bonnett et al., "Dehydroepiandrosterone (DHEA) prevents and reverses chronic hypoxic pulmonary hypertension," *PNAS* 100(16):9488-93 (2003).

Budavari, The Merck Index 11th ed., 1989, pp. 660-661, monograph 4141.

Coleridge et al., "Intravenous aminophylline confers no benefit in acute asthma treated with intravenous steroids and inhaled bronchodilators", *Aust. N.Z. J. Med.* 23:348-54 (1993).

Dashtaki et al., "Dehydroepiandrosterone and Analogs Inhibit DNA Binding of AP-1 and Airway Smooth Muscle Proliferation[1]," *J. Pharmacol. Exp. Thera.* 285(2):876-83 (1998).

Dompeling et al., "Treatment with Inhaled Steroids in Asthma and Chronic Bronchitis: Long Term Compliance and Inhaler Technique", *Family Practice* 9(2):161-6 (1992).

Dunn, et al., "Dehydroepiandrosterone sulphate concentrations in asthmatic patients: pilot study," *N.Z. J. Med.* 97(768):805-8 (1984).

Dworski et al., "Conspectus: Inhaled Steroids in Asthma", *Comprehensive Therapy*, 18:3 (1992).

Fehér et al., "Adrenocortical Function in Bronchial Asthma", *Acta Medica Hungarica* 40(2-3):125-32 (1983).

Fehér, et al., "Dehydroepiandrosterone Therapy of Patients with Corticosteroid Dependent Bronchial Asthma," *Natl. Institute of Rheumatism and Physiotherapy, in XIII Congress of the European Academy of Allergology and Clinical Immunology*, eds. (Saba, et al., Debrecen Hungary (1986).

Hampl et al., "Dehydroepiandrosterone sulphate reduces chronic hypoxic pulmonary hypertension in rats," *J. Eur. Respir.* 21:862-5 (2003).

Holzmann et al., "Therapy of Psoriasis with Dehydroepiandrosterone-Enanthate. II. Intramuscular Depot Application of 300 mg", *Arch. Dermatol. Forsch.* 247(1):23-8 (1973) (German with English Abstract).

Hummel et al., "Comparison of oral-steroid sparing by high-dose and low-dose inhaled steroid in maintenance treatment of severe asthma", *The Lancet*, 340(8834/8835):1483-7 (1992).

Itagaki et al., "Effect of Cortisol on the Release of Human Decidual", *Caplus*, 114875 (1991) (Japanese with English Abstract).

Koó et al., "Our experiences with Dehydroepiandrosterone Therapy in Steroid-Dependent Intrinsic Bronchical Asthma", *Orvosi Hetilap* 128(38):1995-7 (1987) (Hungarian).

Koó et al., "Our experiences with Dehydroepiandrosterone Therapy in Steroid-Dependent Intrinsic Bronchical Asthma", *Orvosi Hetilap* 128(38):1995-7 (1987) (English translation).

Lejeune, "Pathogenesis of Mental Impairment in Trisomy 21", *Annales de Génétique*, 92:27643 (1996) (French with English Abstract).

Mileva et al., "Androstenedione, DHEA sulfate, cortisol, aldosterone and testosterone in bronchial asthma patients", 07608054 (1990) (Russian with English Abstract).

Pashko et al., "Inhibition of 7,12-dimethylbenz(a)anthracene-induced Skin Papillomas and Carcinomas by Dehydroepiandrosterone and 3-beta-methylandrost-5-en-17-one in mice", *Cancer Res.* 45(1):164-6 (1985).

Peeters et al., "Differences in Purine Metabolism in Patients with Down's Syndrome", *J. Intellect. Diabil. Res.* 37:471 (1993). Abstract.

Reed, "Aerosol Steroids as Primary Treatment of Mild Asthma", *New England J. Med.*, 325(6):425-6 (1991).

Rowe et al., "Effectiveness of Steroid Therapy in Acute Exacerbations of Asthma: A Meta-analysis", *Amer. J. Emergency Med.*, 10(4):301-10 (1992).

Sasaki et al., "Cervical Ripening with Dehydroepiandrosterone Sulphate", *Br. J. Obstet. Gynaecol.* 89(3):195-8, (1982).

Sciarra et al., "Aerosols", Remington's Pharmaceutical Sciences, 18th ed. (1990), Eds. Gennaro et al., pp. 1873-1875 and 1694-1712.

Sharma et al., "Screening of potential chemopreventive agents using biochemical markers of carcinogenesis", *Cancer Res.* 54(22):5848-55 (1994).

Shomali, "The Use of Anti-Aging Hormones. Melatonin. Growth Hormone, Testosterone, and Dehydroepiandrosterone: Consumer Enthusiasm for Unproven Therapies", *Md. Med. J.* 46(4):181-6 (1997).

Sonka et al., "Gout and Dehydroepiandrosterone: 3. DHEA Administration", *Endokrynologia Polska* 24(3):209-18 (1973).

Sur et al., "Double-blind trial pyroxidine (vitamin B6) in the treatment of steroid-dependent asthma", *Ann. Allergy*, 70:147-52 (1993).

Schwartz et al., "Inhibition of 7,12-dimethylbenz[a]anthracene- and urethan-induced lung tumor formation in A/J mice by long-term treatment with dehydroepiandrosterone," *Carcinogenesis* 2(12):1335-7 (1981).

Van de Graaf et al., "Respiratory Membrane Permeability and Bronchial Hyperreactivity in Patients with Stable Asthma: Effects of Therapy with Inhaled Steroids", *Bronchial Asthma and Respiratory Membrane Permeability* 143:362-8 (1991).

Van Vollenhoven et al., "Dehydroepiandrosterone in SLE. Results of a Double-Blind, Placebo-Controlled, Randomized Clinical Trial.", *Arthritis Rheum.* 38(12): 1826-31 (1995).

Wolkowitz et al., "Dehydroepiandrosterone Treatment of Depression", *Biol. Psychiatry* 41(3):311-8. (1997).

* cited by examiner

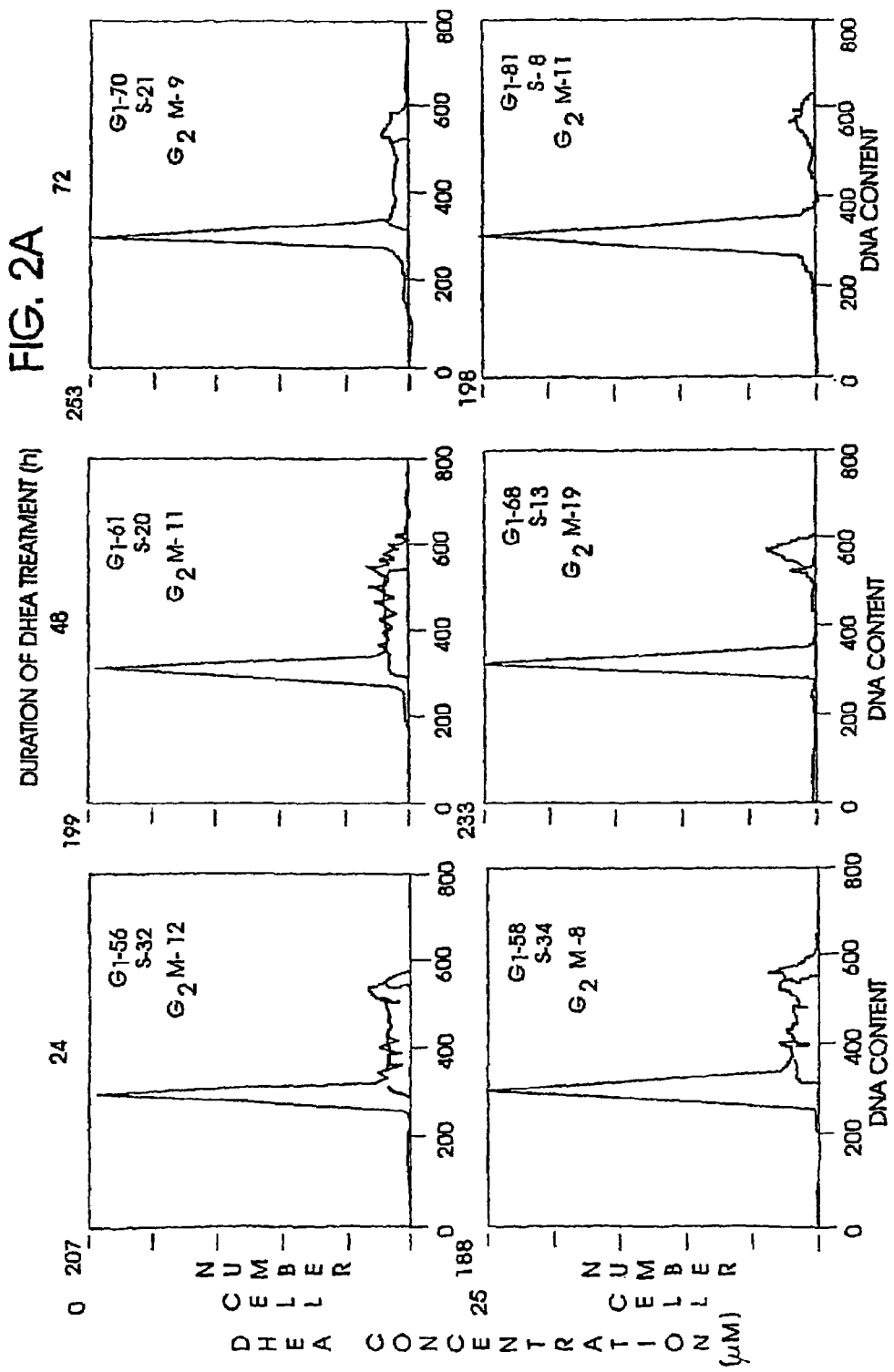

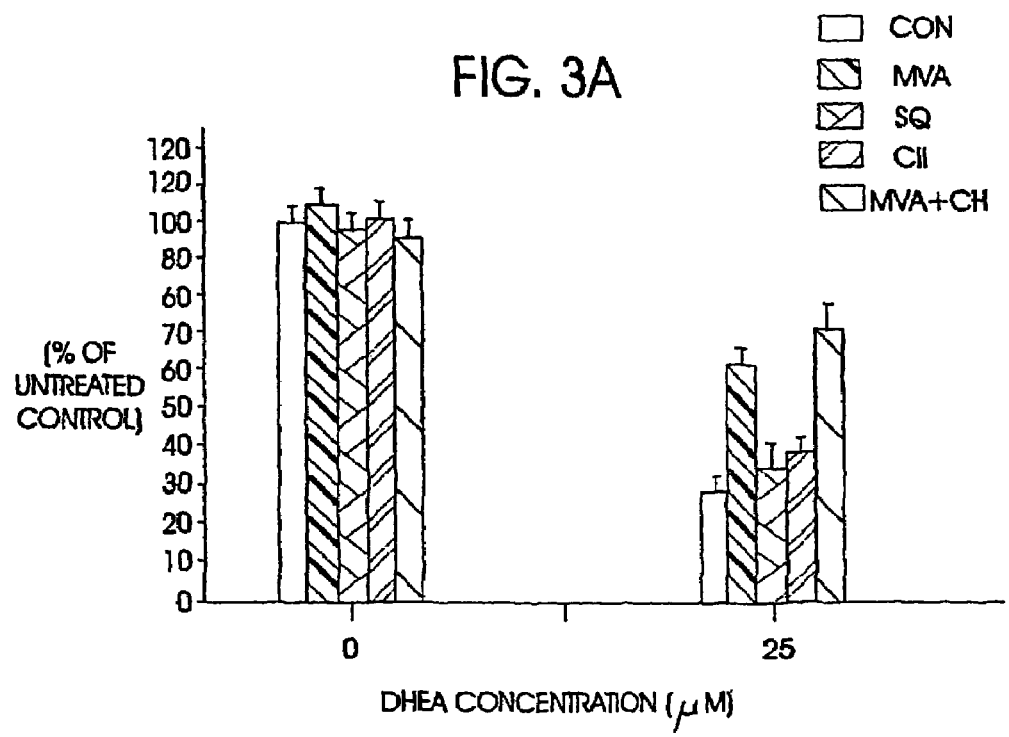
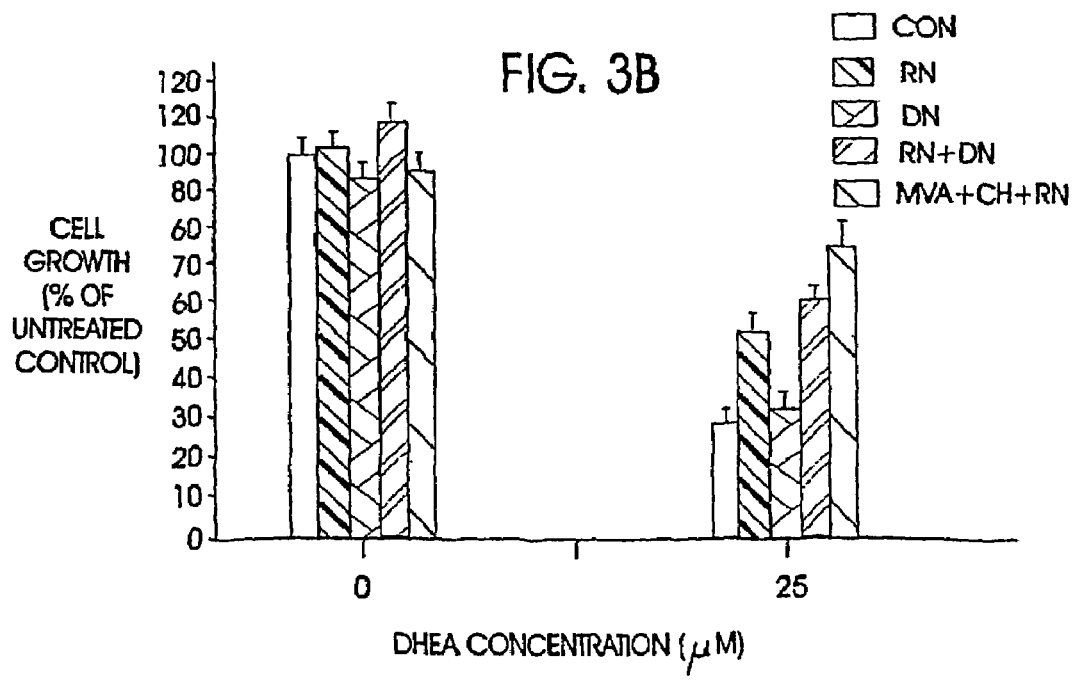

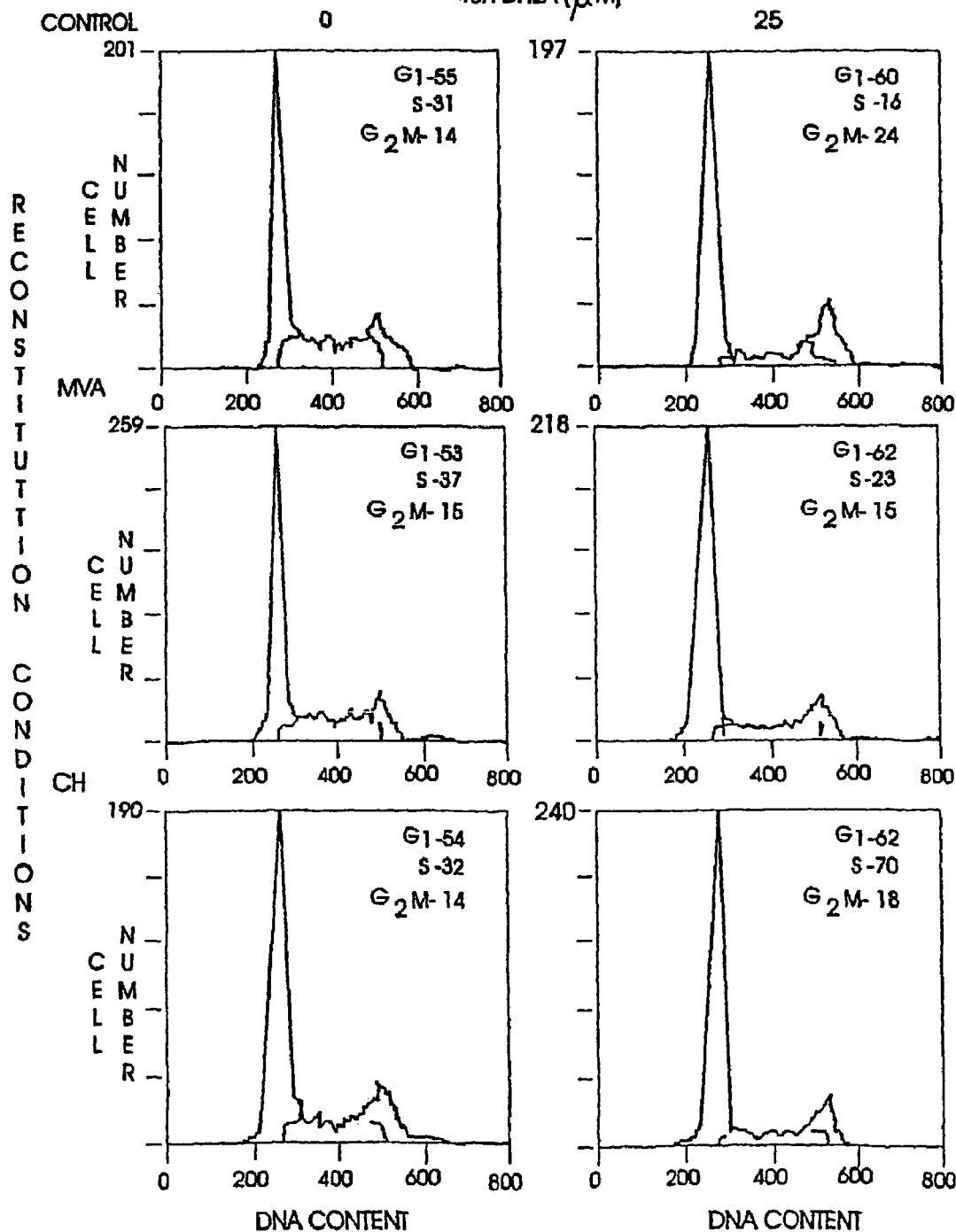

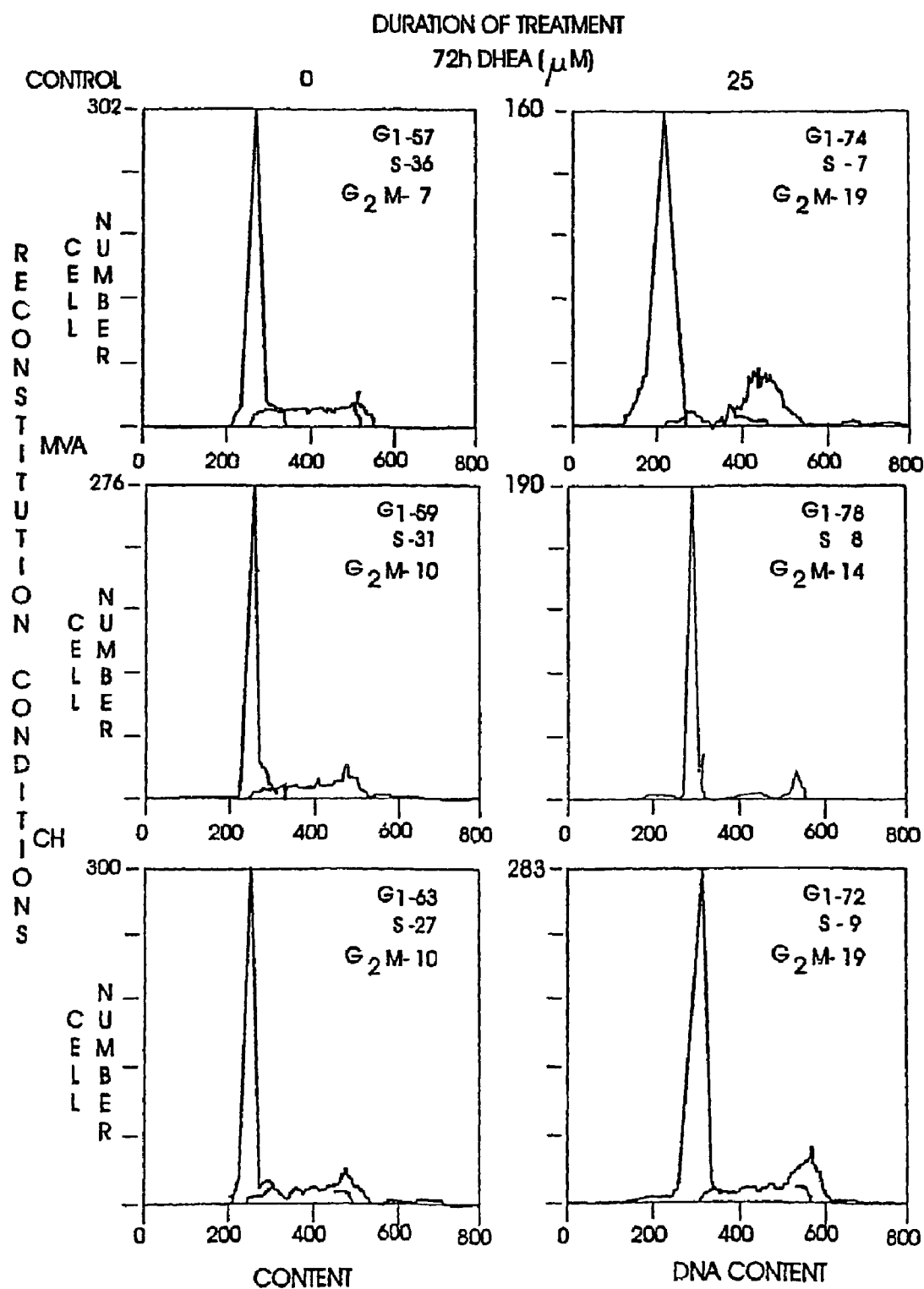

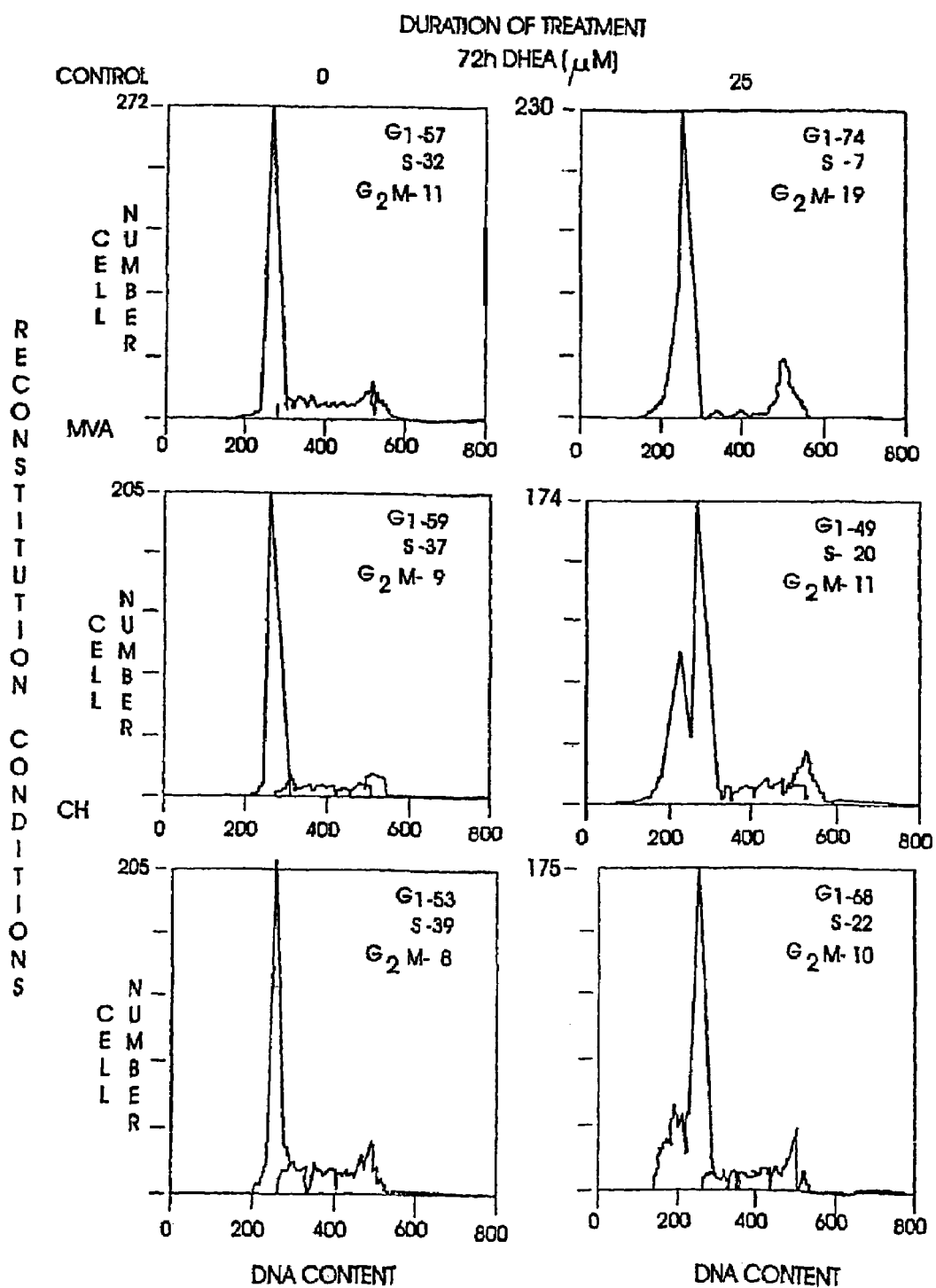

USE OF DHEA AND DHEA-SULFATE FOR THE TREATMENT OF CHRONIC OBSTRUCTIVE PULMONARY DISEASE

This application is a continuation-in-part of International Application No. PCT/US02/12555, filed Apr. 22, 2002, published Oct. 31, 2002 under PCT Article 21(2) in English; which claims priority to U.S. Provisional Application Ser. No. 60/286,124, filed Apr. 24, 2001.

BACKGROUND OF THE INVENTION

1. Field of the Invention

This invention concerns itself with an active agent that is suitable for treating chronic obstructive pulmonary disease (COPD). The present agents may be administered preventatively, prophylactically or therapeutically in conjunction with other therapies, or may be utilized as a substitute for therapies that have significant, negative side effects.

2. Description of the Background

Chronic obstructive pulmonary disease (COPD) causes a continuing obstruction of airflow in the airways. COPD is characterized by airflow obstruction that is generally caused by chronic bronchitis, emphysema, or both. Commonly, the airway obstruction is mostly irreversible. In chronic bronchitis, airway obstruction results from chronic and excessive secretion of abnormal airway mucus, inflammation, bronchospasm, and infection. Chronic bronchitis is also characterized by chronic cough, mucus production, or both, for at least three months in at least two successive years where other causes of chronic cough have been excluded. In emphysema, a structural element (elastin) in the terminal bronchioles is destroyed leading to the collapse of the airway walls and inability to exhale "stale" air. In emphysema there is permanent destruction of the alveoli. Emphysema is characterized by abnormal permanent enlargement of the air spaces distal to the terminal bronchioles, accompanied by destruction of their walls and without obvious fibrosis. COPD can also give rise to secondary pulmonary hypertension. Secondary pulmonary hypertension itself is a disorder in which blood pressure in the pulmonary arteries is abnormally high. In severe cases, the right side of the heart must work harder than usual to pump blood against the high pressure. If this continues for a long period, the right heart enlarges and functions poorly, and fluid collects in the ankles (edema) and belly. Eventually the left heart begins to fail. Heart failure caused by pulmonary disease is called cor pulmonale.

COPD characteristically affects middle aged and elderly people, and is one of the leading causes of morbidity and mortality worldwide. In the United States it affects about 14 million people and is the fourth leading cause of death, and the third leading cause for disability in the United States. Both morbidity and mortality, however, are rising. The estimated prevalence of this disease in the United States has risen by 41% since 1982, and age adjusted death rates rose by 71% between 1966 and 1985. This contrasts with the decline over the same period in age-adjusted mortality from all causes (which fell by 22%), and from cardiovascular diseases (which fell by 45%). In 1998 COPD accounted for 112,584 deaths in the United States.

COPD, however, is preventable, since it is believed that its main cause is exposure to cigarette smoke. Long-term smoking is the most frequent cause of COPD. It accounts for 80 to 90% of all cases. A smoker is 10 times more likely than a non-smoker to die of COPD. The disease is rare in lifetime non-smokers, in whom exposure to environmental tobacco smoke will explain at least some of the airways obstruction. Other proposed etiological factors include airway hyper responsiveness or hypersensitivity, ambient air pollution, and allergy. The airflow obstruction in COPD is usually progressive in people who continue to smoke. This results in early disability and shortened survival time. Stopping smoking reverts the decline in lung function to values for non-smokers. Other risk factors include: heredity, second-hand smoke, exposure to air pollution at work and in the environment, and a history of childhood respiratory infections. The symptoms of COPD include: chronic coughing, chest tightness, shortness of breath, an increased effort to breathe, increased mucus production, and frequent clearing of the throat.

There is very little currently available to alleviate symptoms of COPD, prevent exacerbations, preserve optimal lung function, and improve daily living activities and quality of life. Many patients will use medication chronically for the rest of their lives, with the need for increased doses and additional drugs during exacerbations. Medications that are currently prescribed for COPD patients include: fast-acting $\beta$2-agonists, anticholinergic bronchodilators, long-acting bronchodilators, antibiotics, and expectorants. Amongst the currently available treatments for COPD, short term benefits, but not long term effects, were found on its progression, from administration of anti-cholinergic drugs, $\beta$2 adrenergic agonists, and oral steroids.

Short and long acting inhaled $\beta$2 adrenergic agonists achieve short-term bronchodilation and provide some symptomatic relief in COPD patients, but show no meaningful maintenance effect on the progression of the disease. Short acting $\beta$2 adrenergic agonists improve symptoms in subjects with COPD, such as increasing exercise capacity and produce some degree of bronchodilation, and even an increase in lung function in some severe cases. The maximum effectiveness of the newer long acting inhaled, $\beta$2 adrenergic agonists was found to be comparable to that of short acting $\beta$2 adrenergic agonists. Salmeterol was found to improve symptoms and quality of life, although only producing modest or no change in lung function. In asthmatics, however, $\beta$2 adrenergic agonists have been linked to an increased risk of death, worsened control of asthma, and deterioration in lung function. $\beta$2-agonists, such as albuterol, help to open narrowed airways. The use of $\beta$2-agonists can produce paradoxical bronchospasm, which may be life threatening to the COPD patient. In addition, the use of $\beta$2-agonists can produce cardiovascular effects, such as altered pulse rate, blood pressure and electrocardiogram results. In rare cases, the use of $\beta$2-agonists can produce hypersensitivity reactions, such as urticaria, angioedema, rash and oropharyngeal edema. In these cases, the use of the $\beta$2-agonist should be discontinued. Continuous treatment of asthmatic and COPD patients with the bronchodilators ipratropium bromide or fenoterol resulted in a faster decline in lung function, when compared with treatment provided on a need basis, therefore indicating that they are not suitable for maintenance treatment. The most common immediate adverse effect of $\beta$2 adrenergic agonists, on the other hand, is tremors, which at high doses may cause a fall in plasma potassium, dysrhythmias, and reduced arterial oxygen tension. The combination of a $\beta$2 adrenergic agonist with an anti-cholinergic drug provides little additional bronchodilation compared with either drug alone. The addition of ipratropium to a standard dose of inhaled $\beta$2 adrenergic agonists for about 90 days, however, produces some improvement in stable COPD patients over either drug alone. Anti-cholinergic agents were found to produce greater bronchodilation in combination with anti-cholinergic agents than $\beta$2 adrenergic agonists, in people with COPD. Overall, the occurrence of adverse effects with $\beta$2 adrenergic agonists, such as tremor and dysrhythmias, is more frequent than with anti-cholinergics. Thus, neither anti-cholinergic drugs nor β2 adrenergic agonists have an effect on all people with COPD; nor do the two agents combined.

Anti-cholinergic drugs achieve short-term bronchodilation and produce some symptom relief in people with COPD, but no improved long-term prognosis even with inhaled products. Most COPD patients have at least some measure of airways obstruction that is somewhat alleviated by ipratropium bromide. "The lung health study" found in men and women smokers spirometric signs of early COPD. Three treatments compared over a five year period found that ipratropium bromide had no significant effect on the decline in the functional effective volume of the patient's lungs whereas smoking cessation produced a slowing of the decline in the functional effective volume of the lungs. Ipratropium bromide, however, produced serious adverse effects, such as cardiac symptoms, hypertension, skin rashes, and urinary retention. Anticholinergic bronchodilators, such as ipratropium bromide, and theophylline derivatives, help to open narrowed airways. Long-acting bronchodilators help to relieve constriction of the airways and help prevent bronchospasm associated with COPD. Theophyllines have a small bronchodilatory effect in COPD patients whereas they have some common adverse effects, and they have a small therapeutic range given that blood concentrations of 15-20 mg/l are required for optimal effects. Adverse effects include nausea, diarrhea, headache, irritability, seizures, and cardiac arrhythmias, and they occur at highly variable blood concentrations and, in many people, they occur within the therapeutic range. The theophyllines' doses must be adjusted individually according to smoking habits, infection, and other treatments, which is cumbersome. Although theophyllines have been claimed to have an anti-inflammatory effect in asthma, especially at lower doses, none has been reported in COPD, although their bronchodilating short-term effect appears to be statistically different from placebo. The adverse effects of theophyllines and the need for frequent monitoring limit their usefulness. There is no evidence that anti-cholinergic agents affect the decline in lung function, and mucolytics have been shown to reduce the frequency of exacerbations but with a possible deleterious effect on lung function. The long-term effects of β2 adrenergic agonists, oral corticosteroids, and antibiotics have not yet been evaluated, and up to the present time no other drug has been shown to affect the progression of the disease or survival.

Oral corticosteroids elicit some improvement in baseline functional effective volume in stable COPD patients whereas systemic corticosteroids have been found to be harmful at least producing some osteoporosis and inducing overt diabetes. The longer term administration of oral corticosteroids may be useful in COPD, but their usefulness must be weighed against their substantial adverse effects. Inhaled corticosteroids have been found to have no real short-term effect on airway hyper-responsiveness to histamine, but a small long-term effect on lung function, e.g., in pre-bronchodilator functional effective volume. Fluticasone treatment of COPD patients showed a significant reduction in moderate and severe (but not mild) exacerbations, and a small but significant improvement in lung function and six minute walking distance. Oral prednisolone, inhaled beclomethasone or both had no effects in COPD patients, but lung function improved oral corticosteroids. Mucolytics have a modest beneficial effect on the frequency and duration of exacerbations but an adverse effect on lung function. Neither N-acetylcysteine nor other mucolytics, however, have a significant effect in people with severe COPD (functional effective volume<50%) in spite of evidencing greater reductions in frequency of exacerbation. N-acetylcysteine produced gastrointestinal side effect. Long-term oxygen therapy administered to hypoxaemic COPD and congestive cardiac failure, patients, had little effect on their rates of death for the first 500 days or so, but survival rates in men increased afterwards and remained constant over the next five years. In women, however, oxygen decreased the rates of death throughout the study. Continuous oxygen treatment of hypoxemic COPD patients (functional effective volume<70% predicted) for 19.3 years decreased overall risk of death. To date, however, only life style changes, smoking cessation and long term treatment with oxygen (in hypoxaemics), have been found to alter the long-term course of COPD.

Antibiotics are also often given at the first sign of a respiratory infection to prevent further damage and infection in diseased lungs. Expectorants help loosen and expel mucus secretions from the airways, and may help make breathing easier.

In addition, other medications may be prescribed to manage conditions associated with COPD. These may include: diuretics (which are given as therapy to avoid excess water retention associated right-heart failure), digitalis (which strengthens the force of the heartbeat), painkillers cough suppressants, and sleeping pills. This latter list of medications help alleviate symptoms associated with COPD but do not treat COPD.

Thus, there is very little currently available to alleviate symptoms of COPD, prevent exacerbations, preserve optimal lung function, and improve daily living activities an quality of life.

COPD and other respiratory ailments, associated with a variety of diseases and conditions, are extremely common in the general population, and more so in certain ethnic groups, such as African Americans. In some cases they are accompanied by inflammation, which aggravates the condition of the lungs. Asthma, for example, is one of the most common diseases in industrialized countries. In the United States it accounts for about 1% of all health care costs. An alarming increase in both the prevalence and mortality of asthma over the past decade has been reported, and asthma is predicted to be the preeminent occupational lung disease in the next decade. While the increasing mortality of asthma in industrialized countries could be attributable to the reliance upon beta agonists in the treatment of this disease, the underlying causes of asthma remain poorly understood.

Other respiratory diseases such as asthma, allergic rhinitis, and Acute Respiratory Distress Syndrome (ARDS), including ARDS in pregnant mothers and Respiratory Distress Syndrome (RDS) in premature born infants, pulmonary fibrosis, and cystic fibrosis (CF), among others, are common diseases in industrialized countries, and in the United States alone account for extremely high health care costs. These diseases have recently been increasing at an alarming rate, both in terms of prevalence, morbidity and mortality. In spite of this, their underlying causes still remain poorly understood.

Asthma is a condition characterized by variable, in many instances reversible obstruction of the airways. This process is associated with lung inflammation and in some cases lung allergies. Many patients have acute episodes referred to as "asthma attacks," while others are afflicted with a chronic condition. The asthmatic process is believed to be triggered in some cases by inhalation of antigens by hypersensitive subjects. This condition is generally referred to as "extrinsic asthma." Other asthmatics have an intrinsic predisposition to the condition, which is thus referred to as "instrinsic asthma," and may be comprised of conditions of different origin, including those mediated by the adenosine receptor(s), allergic conditions mediated by an immune IgE-mediated response, and others. All asthmas have a group of symptoms, which are characteristic of this condition: bronchoconstriction, lung inflammation and decreased lung surfactant. Existing bronchodilators and anti-inflammatories are currently commercially available and are prescribed for the treatment of asthma. The most common anti-inflammatories, corticosteroids, have considerable side effects but are commonly prescribed nevertheless. Most of the drugs available for the treatment of asthma are, more importantly, barely effective in a small number of patients. Acute Respiratory Distress Syndrome (ARDS) is also known in the medical literature as stiff lung, shock lung, pump lung and congestive atelectasis, and its incidence is 1 out of 100,000 people. ARDS is believed to be caused by a failure of the respiratory system characterized by fluid accumulation within the lung that, in turn, causes the lung to stiffen. The condition is triggered by a variety of processes that injure the lungs. In general, ARDS occurs as a medical emergency. It may be caused by a variety of conditions that directly or indirectly cause the blood vessels to "leak" fluid into the lungs. In ARDS, the ability of the lungs to expand is severely decreased and damage to the air sacs and lining (endothelium) of the lung is extensive. The concentration of oxygen in the blood remains very low in spite of high concentration of supplemental oxygen that is generally administered to a patient. Among the systemic causes of lung injury are trauma, head injury, shock, sepsis, multiple blood transfusions and medications. Pulmonary causes include pulmonary embolism, severe pneumonia, smoke inhalation, radiation, high altitude, near drowning, and others like cigarette smoking. ARDS symptoms usually develop within 24 to 48 hours of the occurrence of an injury or illness.

ARDS' most common symptoms are labored, rapid breathing, nasal flaring, cyanosis blue skin, lips and nails caused by lack of oxygen to the tissues, breathing difficulty, anxiety, stress, tension, joint stiffness, pain and temporarily absent breathing. ARDS is commonly diagnosed by testing for symptomatic signs, for example by a simple chest auscultation or examination with a stethoscope that may reveal abnormal symptomatic breath sounds. A preliminary diagnosis of ARDS may be confirmed with chest X-rays and the measurement of arterial blood gas. In some cases ARDS appears to be associated with other diseases, such as acute myelogenous leukemia, with acute tumor lysis syndrome (ATLS) developed after treatment with, e.g. cytosine arabinoside. In general, however, ARDS appears to be associated with traumatic injury, severe blood infections such as sepsis, or other systemic illness, high dose radiation therapy and chemotherapy, and inflammatory responses which lead to multiple organ failure, and in many cases death. In premature babies ("premies"), the lungs are not quite developed and, therefore, the fetus is in an anoxic state during development. Moreover, lung surfactant, a material critical for normal respiration, is generally not yet present in sufficient amounts at this early stage of life; however, premies often hyper-express the adenosine $A_1$ receptor and/or underexpress the adenosine $A_{2a}$ receptor and are, therefore, susceptible to respiratory problems including bronchoconstriction, lung inflammation and ARDS, among others. When Respiratory Distress Syndrome (RDS) occurs in premies, it is an extremely serious problem. Preterm infants exhibiting RDS are currently treated by ventilation and administration of oxygen and surfactant preparations. When premies survive RDS, they frequently develop bronchopulmonary dysplasia (BPD), also called chronic lung disease of early infancy, which is often fatal.

The systemic administration of adenosine was found useful for treating SVT, and as a pharmacologic means to evaluate cardiovascular health via an adenosine stress test commonly administered by hospitals and by doctors in private practice. Adenosine administered by inhalation, however, is known to cause bronchoconstriction in asthmatics, possibly due to mast cell degranulation and histamine release, effects which have not been observed in normal subjects. Adenosine infusion has caused respiratory compromise, for example, in patients with COPD. As a consequence of the untoward side effects observed in many patients, caution is recommended in the prescription of adenosine to patients with a variety of conditions, including obstructive lung disease, emphysema, bronchitis, etc, and complete avoidance of its administration to patients with or prone to bronchoconstriction or bronchospasm, such as asthma. In addition, the administration of adenosine must be discontinued in any patient who develops severe respiratory difficulties. It would be of great help if a formulation were to be made available for joint use when adenosine administration is required.

Rhinitis may be seasonal or perennial, allergic or non-allergic. Non-allergic rhinitis may be induced by infections, such as viruses, or associated with nasal polyps, as occurs in patients with aspirin idiosyncrasy. Medical conditions such as pregnancy or hypothyroidism and exposure to occupational factors or medications may cause rhinitis. Allergic rhinitis afflicts one in five Americans, accounting for an estimated $4 to 10 billion in health care costs each year, and occurs at all ages. Because many people mislabel their symptoms as persistent colds or sinus problems, allergic rhinitis is probably underdiagnosed. Typically, IgE combines with allergens in the nose to produce release of chemical mediators, induction of cellular processes, and neurogenic stimulation, causing an underlying inflammation. Symptoms include nasal congestion, discharge, sneezing, and itching, as well as itchy, watery, swollen eyes. Over time, allergic rhinitis sufferers often develop sinusitis, otitis media with effusion, and nasal polyposis, and may exacerbate asthma, and is associated with mood and cognitive disturbances, fatigue and irritability. When cholinergic pathways are stimulated they produce typical secretions that are identified by their glandular constituents so as to implicate neurologic stimulation. Other secretions typical of increased vascular permeability are found in allergic reactions as well as upper respiratory infections, and degranulation of mast cells results in the release of preformed mediators that interact with various cells, blood vessels, and mucous glands to produce the typical rhinitis symptoms. Most early- and late-phase reactions occur in the nose after allergen exposure. The late-phase reaction is seen in chronic allergic rhinitis, with hypersecretion and congestion as the most prominent symptoms. Repeated exposure causes a hypersensitivity reaction to one or many allergens. Sufferers may also become hyperreactive to nonspecific triggers such as cold air or strong odors. Nonallergic rhinitis may be induced by infections, such as viruses, or associated with nasal polyps, as occurs in patients with aspirin idiosyncrasy. In addition, pregnancy, hypothyroidism, and exposure to occupational factors or medications can cause rhinitis, as well. NARES syndrome, a non-allergic type of rhinitis associated with eosinophils in the nasal secretions, typically occurs in middle-aged individuals and is accompanied by loss of smell. Saline is often recommended to improve nasal stuffiness, sneezing, and congestion, and saline sprays usually relieve mucosal irritation or dryness associated with various nasal conditions, minimize mucosal atrophy, and dislodge encrusted or thickened mucus, while causing no side effects, and may be tried first in pregnant patients. Also, if used immediately before intranasal corticosteroid dosing, saline helps prevent local irritation. Anti-histamines often serve as a primary therapy. Terfenadine and astemizole, two non-sedating anti-histamines, however, have been associated with a ventricular arrhythmia known as Torsades de Points, usually in interaction with other medications such as ketoconazole and erythromycin, or secondary to an underlying cardiac problem. To date loratadine, another nonsedating anti-histamine, and cetirizine have not been associated with serious adverse cardiovascular events, the most common side effect of cetirizine being drowsiness. Claritin, for example, may be effective in relieving sneezing, runny nose, and nasal, ocular and palatal itching in a low percentage of patients, although not approved for this indication or asthma. Terfenadine, loratadine and astemizole, on the other hand, exhibit extremely modest bronchodilating effects, reduction of bronchial hyper-reactivity to histamine, and protection against exercise- and antigen-induced bronchospasm. Some of these benefits, however, require higher-than-currently-recommended doses. The sedating-type anti-histamines help induce night sleep, but they cause sleepiness and compromise performance if taken during the day. Anti-histamines are typically combined with a decongestant to help relieve nasal congestion. Sympathomimetic medications are used as vasoconstrictors and decongestants, the three most common decongestants being pseudoephedrine, phenylpropanolamine and phenylephrine. These agents, however, cause hypertension, palpitations, tachycardia, restlessness, insomnia and headache. The interaction of phenylpropanolamine with caffeine, in doses of two to three cups of coffee, may significantly raise blood pressure. In addition, medications such as pseudoephedrine may cause hyperactivity in children. Topical decongestants are recommended for a limited period of time, as their over use results in nasal dilatation. Anticholinergic agents, such as Cromolyn, have a role in patients with significant rhinorrhea or for specific entities such as "gustatory rhinitis", which is usually associated with ingestion of spicy foods, and have been used on the common cold. However, sometimes the Cromolyn spray produces sneezing, transient headache, and even nasal burning. Topical and nasal spray corticosteroids such as Vancenase are effective agents in the treatment of rhinitis, especially for symptoms of congestion, sneezing, and runny nose, but often cause irritation, stinging, burning, sneezing, local bleeding and septal perforation. Topical steroids are generally more effective than Cromolyn Sodium, particularly in the treatment of NARES, but side effects limit their usefulness except for temporary therapy in patients with severe symptoms. These agents are sometimes used for shrinking nasal polyps when local therapy fails. Immunotherapy, while expensive and inconvenient, often can provide substantial benefits, especially the use of drugs that produce blocking antibodies, alter cellular histamine release, and result in decreased IgE. Presently available treatments, such as propranolol, verapamil, and adenosine (all of which have FDA-approved labeling for acute termination of supraventricular tachycardia (SVT)), may help to minimize symptoms. Verapamil is most commonly used but it has several shortcomings, since it causes or exacerbates systemic hypotension, congestive heart failure, bradyarrhythmias, and ventricular fibrillation. In addition, verapamil readily crosses the placenta and has been shown to cause fetal bradycardia, heart block, depression of contractility, and hypotension. Adenosine has several advantages over verapamil, including rapid onset, brevity of side effects, theoretical safety, and probable lack of placental transfer, but may not be administered to a variety of patients.

Pulmonary fibrosis, interstitial lung disease (ILD), or interstitial pulmonary fibrosis, include more than 130 chronic lung disorders that affect the lung by damaging lung tissue, and producing inflammation in the walls of the air sacs in the lung, scarring or fibrosis in the interstitium (or tissue between the air sacs), and stiffening of the lung, thus the name of the disease. Although the progress and symptoms of pulmonary fibrosis and other ILDs may vary from person to person, they have one common link: they affect parts of the lung. When inflammation involves the walls of the bronchioles (small airways), it is called bronchiolitis, when it involves the walls and air spaces of the alveoli (air sacs), it is called alveolitis, and when it involves the small blood vessels (capillaries) of the lungs, it is called vasculitis. The inflammation may heal, or it may lead to permanent scarring of the lung tissue, in which case it is called pulmonary fibrosis. This fibrosis or scarring of the lung tissue results in permanent loss of its ability to breathe and carry oxygen, and the amount of scarring determines the level of disability a person experiences because of the destruction by the scar tissue of the air sacs and lung tissue between and surrounding the air sacs and the lung capillaries. When this happens, oxygen is generally administered to help improve breathing. Pulmonary fibrosis is caused by, or takes the form of, occupational and environmental exposure to irritants such as asbestos, silica and metal dusts, bacteria and animal dusts, gases and fumes, asbestosis and silicosis, infections that produce lung scarring, of which tuberculosis is one example, connective tissue or collagen diseases such as Rheumatoid Arthritis, Systemic Sclerosis and Systemic Lupus Erythematosis, idiopathic pulmonary fibrosis and, although not as common, pulmonary fibrosis of genetic/familial origin and certain medicines. Many of the diseases are often named after the occupations with which they are associated, such as Grain handlier's lung, Mushroom worker's lung, Bagassosis, Detergent worker's lung, Maple bark stripper's lung, Malt worker's lung, Paprika splitter's lung, and Bird breeder's lung. "Idiopathic" (of unknown origin) pulmonary fibrosis (IPF) is the label applied when all other causes of interstitial lung disease have been ruled out, and is said to be caused by viral illness and allergic or environmental exposure (including tobacco smoke). Bacteria and other microorganisms are not thought to be a cause of IPF. There is also a familial form of the disease, known as familial idiopathic pulmonary fibrosis whose main symptom is shortness of breath. Since many lung diseases show this symptom, making a correct diagnosis is often difficult. The shortness of breath may first appear during exercise and the condition may progress then to the point where any exertion is impossible. Eventually resulting in shortness of breath even at rest. Other symptoms may include a dry cough (without sputum), and clubbing of the fingertips. Glucocorticosteroids are usually administered to treat inflammation present in pulmonary fibrosis, with inconclusive results. Other drugs, however, are not usually added until it is clear that the steroids are not effective in reversing the disease. Glucocorticosteroids are also used in combination with other drugs when a diagnosis is first established, for example oxygen therapy prescribed in severe cases. The administration of influenza and pneumococcal pneumonia vaccines is often recommended in pulmonary fibrosis and more generally for all lung diseases to prevent infection. The treatment and management of pulmonary fibrosis often requires a lung biopsy to assess the unpredictable response of patients to glucocorticosteroids or other immune system suppressants. Lung transplants are sometimes an ultimate option in severe cases of pulmonary fibrosis and other lung diseases. Pulmonary fibrosis may also be caused by other specific diseases, such as sarcoidosis, a disease whose cause is unknown, that is characterized by the formation of granulomas or areas of inflammatory cells. The disease may attack any organ of the body, but most frequently attacks the lungs, and is generally diagnosed when a chest x-ray shows enlarged lymph glands in the center of both lungs or evidence of lung tissue thickening. For many sarcoidosis is a minor problem, and symptoms including dry cough, shortness of breath, mild chest pain, fatigue, weakness and weight loss-may appear infrequently and stop even without medication. For others, it is a serious, disabling disease that affects African-Americans more than members of any other race, although almost everybody may develop the disease, most common in young adults 20 to 40. Histiocytosis X, also associated with pulmonary fibrosis, seems to begin in the bronchioles or small airways of the lungs and their associated arteries and veins, and is generally followed by destruction of the bronchioles and narrowing and damaging of small blood vessels. It is diagnosed by a bronchoalveolar lavage test involving the removal and identification of cells from the lower respiratory tract. Symptoms of this disease include a dry cough (without sputum), breathlessness upon exertion, and/or chest pain. In approximately 50% of the cases, the disease is chronic with loss of lung function, and although glucocorticosteroid therapy is often prescribed, there is no evidence that it is effective. Many histiocytosis X sufferers are current or former cigarette smokers, although its association with smoking is not well understood. Many jobs, particularly those that involve mining or that expose workers to asbestos or metal dusts, may cause pulmonary fibrosis by inhalation of small particulate matter, e.g., dust or asbestos fibers that damage the lungs, especially the small airways and air sacs, and cause scarring (fibrosis). Agricultural workers are also affected by some particulate organic substances, such as moldy hay, which cause an allergic reaction in the lung called "Farmer's Lung", and may cause pulmonary fibrosis as well. Asbestosis and silicosis are two occupational lung diseases whose causes are known. Asbestosis is caused by small needle-like particles of asbestos inhaled into the lungs, and cause lung scarring or pulmonary fibrosis that may lead to lung cancer. Silicosis is a dust disease that comes from breathing in free crystalline silica dust, and is produced by all types of mining in which the ore, e.g. gold, lead, zinc, copper, iron, anthracite (hard) coal, and some bituminous (soft) coal, are extracted from quartz rock. Workers in foundries, sandstone grinding, tunneling, sandblasting, concrete breaking, granite carving, and china manufacturing also encounter silica. Large silica particles are stopped in the upper airways, but the tiniest specks of silica are carried down to the lung alveoli, where they lead to pulmonary fibrosis. The use of glucocorticosteroids alone, or combined drug therapy, and the hope of lung transplant are three treatment approaches that are currently being tested, but up to the present time there is no good therapy for this disease. This patent provides the first effective therapy for these and other respiratory and lung ailments.

Cancer is one of the most prevalent and feared diseases of our times. It generally results from the carcinogenic transformation of normal cells of different epithelia. Two of the most damaging characteristics of carcinomas and other types of malignancies are their uncontrolled growth and their ability to create metastases in distant sites of the host, particularly a human host. It is usually these distant metastases that may cause serious consequences to the host since, frequently, the primary carcinoma is removed by surgery. The treatment of cancer presently relies on surgery, irradiation therapy and systemic therapies such as chemotherapy, different immunity-boosting medicines and procedures, hyperthermia and systemic, radioactively labeled monoclonal antibody treatment, immunotoxins and chemotherapeutic drugs.

Dehydroepiandrosterone (DHEA) is a naturally occurring steroid secreted by the adrenal cortex with apparent chemoprotective properties. Epidemiological studies have shown that low endogenous levels of DHEA correlate with increased risk of developing some forms of cancer, such as pre-menopausal breast cancer in women and bladder cancer in both sexes. The ability of DHEA and DHEA analogues, e.g. dehydroepiandrosterone sulfate (DHEA-S), to inhibit carcinogenesis is not clear but one suggestion is that it results from their non-competitive inhibition of the activity of the enzyme glucose 6-phosphate dehydrogenase (G6PDH). G6PDH is the rate limiting enzyme of the hexose monophosphate pathway, a major source of intracellular ribose-5-phosphate and NADPH. Ribose-5-phosphate is a necessary substrate for the synthesis of both ribo- and deoxyribonucleotides required for the synthesis of RNA and DNA. NADPH is a cofactor also involved in nucleic acid biosynthesis and the synthesis of hydroxmethylglutaryl Coenzyme A reductase (HMG CoA reductase). HMG CoA reductase is an unusual enzyme that requires two moles of NADPH for each mole of product, mevalonate, produced. Thus, it appears that HMG CoA reductase would be ultrasensitive to DHEA-mediated NADPH depletion, and that DHEA-treated cells would rapidly show the depletion of intracellular pools of mevalonate. Mevalonate is required for DNA synthesis, and DHEA arrests human cells in the G1 phase of the cell cycle in a manner closely resembling that of the direct HMG CoA. Because G6PDH produces mevalonic acid used in cellular processes such as protein isoprenylation and the synthesis of dolichol, a precursor for glycoprotein biosynthesis, DHEA inhibits carcinogenesis by depleting mevalonic acid and thereby inhibiting protein isoprenylation and glycoprotein synthesis. Mevalonate is a central precursor for the synthesis of cholesterol, as well as for the synthesis of a variety of non-sterol compounds involved in post-translational modification of proteins, such as farnesyl pyrophosphate and geranyl pyrophosphate. Mevalonate is also a central precursor for the synthesis of dolichol, a compound that is required for the synthesis of glycoproteins involved in cell-to-cell communication and cell structure. Mevalonate is also central to the manufacture of ubiquinone, an anti-oxidant with an established role in cellular respiration. It has long been known that patients receiving steroid hormones of adrenocortical origin at pharmacologically appropriate doses show increased incidence of infectious disease.

DHEA, also known as (3β)-3-hydroxyandrost-5-en-17-one, or dehydroisoandrosterone, is a 17-ketosteroid which is quantitatively one of the major adrenocortical steroid hormones found in mammals. Although DHEA appears to serve as an intermediary in gonadal steroid synthesis, the primary physiological function of DHEA has not been fully understood. It has been known, however, that levels of this hormone begin to decline in the second decade of life, reaching 5% of the original level in the elderly. Clinically, DHEA has been used systemically and/or topically for treating patients suffering from psoriasis, gout, hyperlipemia, and it has been administered to post-coronary patients. In mammals, DHEA has been shown to have weight optimizing and anti-carcinogenic effects, and it has been used clinically in Europe in conjunction with estrogen as an agent to reverse menopausal symptoms and also has been used in the treatment of manic depression, schizophrenia, and Alzheimer's disease. DHEA has also been used clinically at 40 mg/kg/day in the treatment of advanced cancer and multiple sclerosis. Mild androgenic effects, hirsutism, and increased libido were the side effects observed. These side effects can be overcome by monitoring the dose and/or by using analogues. The subcutaneous or oral administration of DHEA to improve the host's response to infections is known, as is the use of a patch to deliver DHEA. DHEA is also known as a precursor in a metabolic pathway that ultimately leads to more powerful agents that increase immune response in mammals. That is, DHEA acts as a biphasic compound: it acts as an immuno-modulator when converted to androstenediol or androst-5-ene-3β,17β-diol (βAED), or androstenetriol or androst-5-ene-3β,7β,17β-triol (βAET). However, in vitro DHEA has certain lymphotoxic and suppressive effects on cell proliferation prior to its conversion to βAED and/or βAET. It is, therefore, believed that the superior immunity enhancing properties obtained by administration of DHEA result from its conversion to more active metabolites.

Adequate ubiquinone levels have been found to be essential for maintaining proper cardiac function, and the administration of exogenous ubiquinone has recently been shown to have beneficial effect in patients with chronic heart failure. Ubiquinone depletion has been observed in humans and animals treated with lovastatin, a direct HMG CoA reductase inhibitor. Such lovastatin-induced depletion of ubiquinone has been shown to lead to chronic heart failure, or to a shift from low heart failure into life-threatening high grade heart failure. DHEA, unlike lovastatin, inhibits HMG CoA reductase indirectly by inhibiting G6PDH and depleting NADPH, a required cofactor for HMG CoA reductase. However, DHEA's indirect inhibition of HMG CoA reductase suffices to deplete intracellular mevalonate, and may result in depletion of ubiquinone, and in chronic heart failure following long term usage.

Adenosine may constitute an important mediator in the lung for various diseases, including bronchial asthma, COPD, CF, RDS, rhinitis, pulmonary fibrosis, and others. Its potential role was suggested by the finding that asthmatics respond favorably to aerosolized adenosine with marked bronchoconstriction whereas normal individuals do not. An asthmatic rabbit animal model, the dust mite allergic rabbit model for human asthma, responded in a similar fashion to aerosolized adenosine with marked bronchoconstriction whereas non-asthmatic rabbits showed no response. More recent work with this animal model suggested that adenosine-induced bronchoconstriction and bronchial hyperresponsiveness in asthma may be mediated primarily through the stimulation of adenosine receptors. Adenosine has also been shown to cause adverse effects, including death, when administered therapeutically for other diseases and conditions in subjects with previously undiagnosed hyper reactive airways.

Adenosine is a purine that contributes to intermediary metabolism and participates in the regulation of physiological activity in a variety of mammalian tissues. Adenosine participates in many local regulatory mechanisms, such as those occurring in synapses in the central nervous system (CNS) and at neuroeffector junctions in the peripheral nervous system. In the CNS, adenosine inhibits the release of a variety of neurotransmitters, such as acetylcholine, noradrenaline, dopamine, serotonin, glutamate, and GABA; depresses neurotransmission; reduces neuronal firing to induce spinal analgesia and possesses anxiolytic properties. In the heart, adenosine suppresses pacemaker activity, slows AV conduction, possesses antiarrhythmic and arrhythmogenic effects, modulates autonomic control and triggers the synthesis and release of prostaglandins. In addition, adenosine has potent vasodilatory effects and modulates vascular tone. Adenosine is currently being used clinically for the treatment of super ventricular tachycardia and other cardia anomalies. Adenosine analogues also are being investigated for use as anticonvulsant, anxiolytic and neuro protective agents. Adenosine has also been implicated as a primary determinant underlying the symptoms of bronchial asthma and other respiratory diseases, the induction of bronchoconstriction and the contraction of airway smooth muscle. Moreover, adenosine causes bronchoconstriction in asthmatics but not in non-asthmatics. Other data suggest the possibility that adenosine receptors may also be involved in allergic and inflammatory responses by reducing the hyperactivity of the central dopaminergic system. It has been postulated that the modulation of signal transduction at the surface of inflammatory cells influences acute inflammation. Adenosine is said to inhibit the production of super-oxide by stimulated neutrophils.

Clearly, there exists a well defined need for novel and effective therapies for treating COPD and other respiratory and lung ailments that cannot presently be treated, or at least for which no therapies are available that are effective and devoid of significant detrimental side effects. This is the case of ailments afflicting the respiratory tract, and more particularly the lung and the lung airways, including respiratory problems, bronchoconstriction, lung inflammation and allergies, depletion or hyposecretion of surfactant, etc. Moreover, there is a definite need for treatments that have prophylactic and therapeutic applications, and require low amounts of active agents, which makes them both less costly and less prone to detrimental side effects. Furthermore, it is readily apparent that the administration of a non-glucocorticoid steroid and/or ubiquinone or their respective salts, is useful for the treatment of respiratory, lung and malignant diseases such as bronchoconstriction, decreased or depleted lung surfactant, asthma, RDS, ARDS, rhinitis, chronic obstructive pulmonary disease (COPD), cystic fibrosis (CF), dyspnea, emphysema, pulmonary hypertension, pulmonary fibrosis, hyper-responsive airways, particularly conditions associated with infectious diseases, lung allergies and inflammation, neoplastic diseases such as lung cancer, and the like.

U.S. Pat. No. 5,527,789 discloses a method of combating cancer in a subject by administering to the subject dehydroepiandrosterone (DHEA) or DHEA-related compound, and ubiquinone to combat heart failure induced by the DHEA or DHEA-related compound. U.S. Pat. No. 6,087,351 discloses an in vivo method of reducing or depleting adenosine in a subject's tissue by administering to the subject dehydroepiandrosterone (DHEA) or DHEA-related compound. However, these patents do not teach using DHEA or DHEA-related compounds to prevent or treat COPD.

SUMMARY OF THE INVENTION

The present invention provides for a method for treating or preventing COPD comprising administering to a subject need of such treatment or prophylaxis a pharmaceutical composition. The pharmaceutical composition comprises a therapeutically effective amount of an active agent suitable for prophylactic and therapeutic treatment of COPD, or any respiratory, lung or cancer disease, the active agent comprising a non-glucocorticoid steroid of the chemical formula

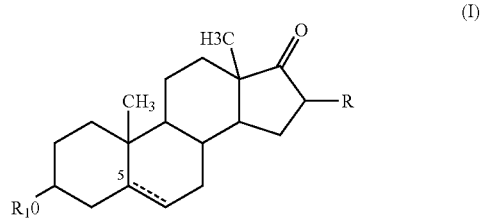

wherein the broken line represents a single or preferably a double bond; R is hydrogen or a halogen; in the case of a single bond the H at position 5 is present in the alpha or beta configuration or the compound of formula I comprises a racemic mixture of both configurations; and $R^1$ is hydrogen or $SO_2OM$, wherein M is selected from the group consisting of H, Na, sulphatide

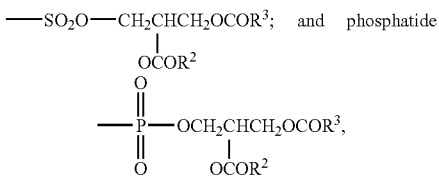 and phosphatide

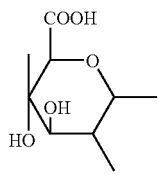

wherein $R^2$ and $R^3$, which may be the same or different, are straight or branched $(C_1-C_{14})$alkyl or glucuronide

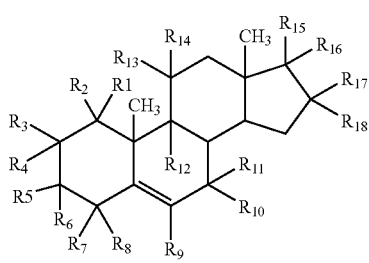

; or a non-glucocorticoid steroid of the chemical formula

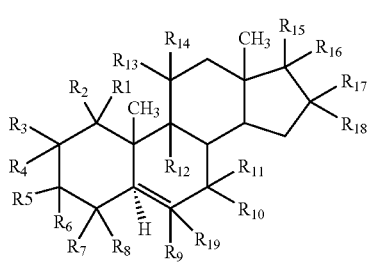

(III)

or a non-glucocorticoid steroid of the chemical formula

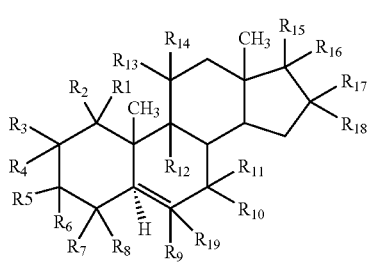

(IV)

wherein R1, R2, R3, R4, R5, R7, R8, R9, R10, R11, R12, R13, R14 and R19 are independently H, OR, halogen, $(C_1-C_{10})$ alkyl or $(C_1-C_{10})$ alkoxy, R5 and R11 are independently OH, SH, H, halogen, pharmaceutically acceptable ester, pharmaceutically acceptable thioester, pharmaceutically acceptable other, pharmaceutically acceptable thioether, pharmaceutically acceptable inorganic esters, pharmaceutically acceptable monosaccharide, disaccharide or oligosaccharide, spirooxirane, spirothirane, —OSO2R20, —OPOR20R21 or $(C_1-C_{10})$ alky, R5 and R6 taken together are =O, R10 and R11 taken together are =O; R15 is (1) H, halogen, $(C_1-C_{10})$ alkyl, or $(C_1-C_{10})$ alkoxy when R16 is —C(O)OR22, (2) H, halogen, OH or $(C_1-C_{10})$ alkyl when R16 is halogen, OH or $(C_1-C_{10})$ alkyl, (3) H, halogen, $(C_1-C_{10})$ alkyd $(C_1-C_{10})$ alkenyl, $(C_1-C_{10})$ alkynyl, formyl, $(C_1-C_{10})$ alkanoyl or epoxy when R16 is OH, (4) or, SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO2R20 or —OPOR20R21 when R16 is H, or R15 and R16 taken together are =O; R17 and R18 are independently (1) H, —OH, halogen, $(C_1-C_{10})$ alkyl or $(C_1-C_{10})$ alkoxy when R6 is H, OH, halogen, $(C_1-C_{10})$ alkyl or —C(O)OR22, (2) H, $(C_1-C_{10})$ alkyl amino, $((C_1-C_{10})$ alkyl)n amino-$(C_1-C_{10})$ alkyl, $(C_1-C_{10})$ alkoxy, hydroxy-$(C_1-C_{10})$ alkyl, $(C_1-C_{10})$ alkoxy-$(C_1-C_{10})$ alkyl, (halogen)m $(C_1-C_{10})$ alkyl, $(C_1-C_{10})$ alkanoyl, formyl, $(C_1-C_{10})$ carbalkoxy or $(C_1-C_{10})$ alkanoyloxy when R15 and R16 taken together are =O, (3) R17 and R18 taken together are =O, (4) R17 or R18 taken together with the carbon to which they are attached form a 3-6 member ring containing 0 or 1 oxygen atom; or (5) R15 and R17 taken together with the carbons to which they are attached form an epoxide ring; R20 and R21 are independently OH, pharmaceutically acceptable ester or pharmaceutically acceptable ether; R22 is H, (halogen)m $(C_1-C_{10})$ alkyl or $(C_1-C_{10})$ alkyl; n is 0, 1 or 2; and m is 1, 2 or 3; or pharmaceutically or veterinarily acceptable salts thereof; and/or a ubiquinone of the chemical formula

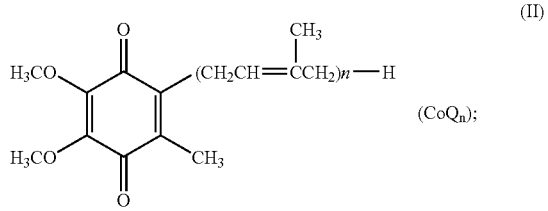

(II)

(CoQ$_n$);

wherein n=1 to 12, the agent being present in an amount effective for treating respiratory lung diseases and conditions, or for reducing levels of, or sensitivity to, adenosine or for increasing surfactant or ubiquinone levels in a subject's tissue (s); or pharmaceutically acceptable salts of either of them. Preferably, the pharmaceutical composition further comprises a pharmaceutically acceptable carrier or diluent.

The active agent described above is provided as a composition and various systemic and topical formulations as well as in a method for the prevention and treatment of COPD, and various respiratory lung diseases and conditions described below.

The present invention also provides for the use of a non-glucocorticoid steroid, analogues thereof, and/or a ubiquinone, or their salts, described above, for the manufacture of a medicament for treating COPD, and other respiratory diseases and conditions.

The present invention also provides for a delivery kit comprising the pharmaceutical composition or active agent described above, and a delivery device. Preferably, the delivery device comprises an inhaler provided with an aerosol or spray generating means that delivers particles about 0.05 to about 10 micron in size or about 10 to about 100 micron in size.

The drawings accompanying this patent form part of the disclosure of the invention, and further illustrate some aspects of the present invention as discussed below.

BRIEF DESCRIPTION OF THE DRAWINGS

FIGS. 2A and 2B illustrate the effects of DHEA on cell cycle distribution in HT-29 SF cells. After 24, 48, and 72 hours, cells were harvested, fixed in ethanol, and stained with propidium iodide, and the DNA content/cell was determined by flow cytometric analysis. The percentage of cells in $G_1$, S, and $G_2M$ phases was calculated using the Cellfit cell cycle analysis program. S phase is marked by a quadrangle for clarity. Representative histograms from duplicate determinations are shown. The experiment was repeated three times.

FIGS. 3A and 3B illustrate the reversal of DHEA-induced growth inhibition in HT-29 cells. In A, the medium was supplemented with 2 μM MVA, 80 μM SQ, 15 μg/ml CH, or MVA plus CH (MVA+CH) or was not supplemented (CON). In B, the medium was supplemented with a mixture of RN containing uridine, cytidine, adenosine, and guanosine in final concentrations of 30 μM each; a mixture of DN containing thymidine, deoxycytidine, deoxyadenosine and deoxyguanosine in final concentrations of 20 μM each; RN plus DN (RN+DN); or MVA plus CH plus RN (MVA+CH+RN). Cell numbers were assessed before and after 48 hours of treatment, and culture growth was calculated as the increase in cell number during the 48 hour treatment period. Columns represent cell growth percentage of untreated controls; bars represent SEM. Increase in cell number in untreated controls was 173,370"6518. Each data point represents quadruplicate dishes from four independent experiments. Statistical analysis was performed using Student's t test $\psi$ p<0.01; κ p, 0.001; compared to treated controls. Note that supplements had little effect on culture growth in absence of DHEA.

FIGS. 4A to 4D illustrate the reversal of DHEA-induced G, arrest in HT-29 SF cells. Cells were plated ($10^5$ cells/60 mm dish) and 48 hours later treated with either 0 or 25 FM DHEA. The medium was supplemented with 2 FM MVA; 15 Fg/ml CH; a mixture of RN containing uridine, cytidine, adenosine, and guanosine in final concentrations of 30 FM; MVA plus CH (MVA+CH); or MVA plus CH plus RN (MVA+CH+RN) or was not supplemented. Cells were harvested after 48 or 72 hours, fixed in ethanol, and stained with propidium iodine, and the DNA content per cell was determined by flow cytometric analysis. The percentage of cells in $G_1$, S, and $G_2M$ phases were calculated using the Cellfit cell cycle profile analysis program. S phase is marked by a quadrangle for clarity. Representative histograms from duplicative determinations are shown. The experiment was repeated two times. Note that supplements had little effect on cell cycle progression in the absence of DHEA.

DETAILED DESCRIPTION OF THE PREFERRED EMBODIMENTS

Figure 1:
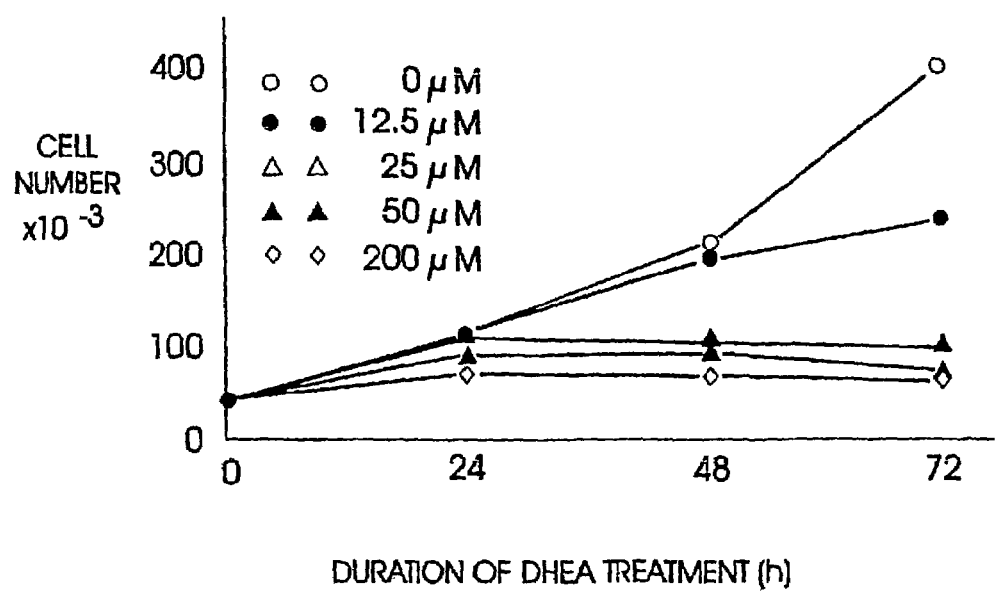
FIG. 1 illustrates the inhibition of HT-29 SF cells by DHEA. Points refer to numbers of cells, and bars refer to SEM. Each data point was performed in quadruplicate, and the experiment was repeated three times. Where SEM bars are not apparent, SEM was smaller than symbol. Exposure to DHEA resulted in a reduced cell number compared to controls after 72 hours in 12.5 UM, 48 hours in 25 or 50 μM, and 24 hours in 200 μM DHEA, indicating that DHEA produced a time- and dose-dependent inhibition of growth.

This invention arose from a desire of the inventor to provide improved prophylactic and therapeutic treatments never before available for COPD and other respiratory and lung diseases and conditions, or treatments that are a substantial improvement over those presently available. The availability of a novel strategy to prevent and/or treat COPD and other disorders and conditions associated with symptoms such as pulmonary bronchoconstriction, impeded respiration, and lung inflammation and allergy(ies), among others, is of great practical importance. Such technology is clearly applicable to the treatment of heart, brain, lung, kidney, skin and other conditions, e.g. ailments associated with hypoxia, infantile Respiratory Disorder Syndrome (RDS), Acute Respiratory Disorder Syndrome (ARDS), aging, cardiac disease, cardiovascular problems, asthma, respiratory distress syndrome, rhinitis, pain, cystic fibrosis (CF), pulmonary hypertension, pulmonary vasoconstriction, pulmonary fibrosis, emphysema, allergic rhinitis, and cancers such as lung cancer, leukemias, lymphomas, carcinomas, and the like, including colon cancer, breast cancer, lung cancer, pancreatic cancer, hepatocellular carcinoma, kidney cancer, melanoma, etc., as well as all types of cancers which may metastasize or have metastasized to the lung(s), including breast, liver and prostate cancer, would clearly find an immediate therapeutic application. Similarly, a composition and method which are suitable for regular administration during a subject's daily routine, and that may be effectively administered preventatively, prophylactically and therapeutically, in conjunction with other therapies, or by itself for conditions without known therapies or as a substitute for therapies that have significant negative side effects is also of immediate clinical application. As the life span of the world population increases, many of these diseases have become more prevalent. Given the more advanced age of a great segment of the population, the advent of new products and preventative and therapeutic treatments would be significantly beneficial.

The present invention provides the use of an active agent suitable for prophylaxis and therapeutic treatment of COPD, and other respiratory, lung and other diseases, selected from a non-glucocorticoid steroid of the chemical formula

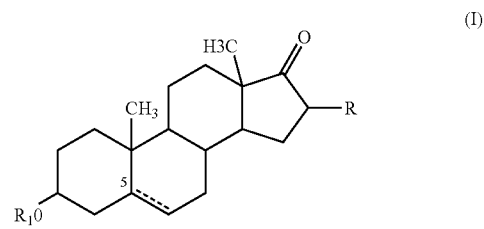

(I)

Epiandrosterone (EA), wherein the broken line represents a single or a double bond; R is hydrogen or a halogen; the H at position 5 is present in the alpha or beta configuration or the compound of formula I comprises a racemic mixture of both configurations; and $R^1$ is hydrogen or $SO_2OM$, wherein M is selected from the group consisting of H, Na, sulphatide

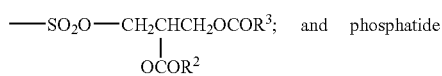

and phosphatide

-continued

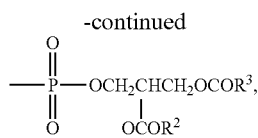

wherein $R^2$ and $R^3$, which may be the same or different, are straight or branched ($C_1$-$C_{14}$) alkyl or glucuronide

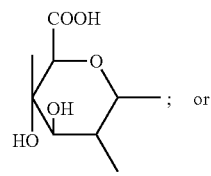

a non-glucocorticoid steroid of the chemical formula

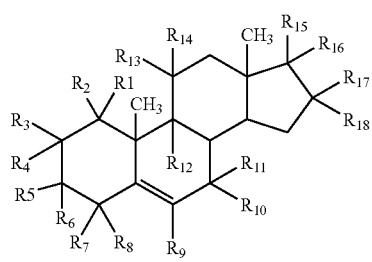

(III)

or a non-glucocorticoid steroid of the chemical formula

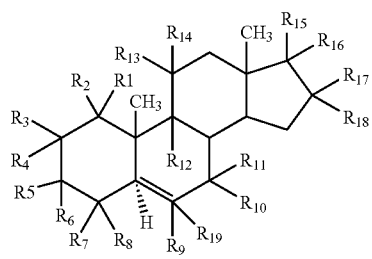

(IV)

wherein R1, R2, R3, R4, R5, R7, R8, R9, R0, R12, R13, R14 and R19 are independently H, OR, halogen, ($C_1$-$C_{10}$) alkyl or ($C_1$-$C_{10}$) alkoxy, R5 and R11 are independently OH, SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO2R20, —OPOR20R21 or ($C_1$-$C_{10}$) alky, R5 and R6 taken together are =O, R10 and R11 taken together are =O; R15 is (1) H, halogen, ($C_1$-$C_{10}$) alkyl, or ($C_1$-$C_{10}$) alkoxy when R16 is —C(O)OR22, (2) H, halogen, OH or ($C_1$-$C_{10}$) alkyl when R16 is halogen, OH or ($C_1$-$C_{10}$) alkyl, (3) H, halogen, ($C_1$-$C_{10}$) alkyl, ($C_1$-$C_{10}$) alkenyl, ($C_1$-$C_{10}$) alknyl, formyl, ($C_1$-$C_{10}$) alkanoyl or epoxy when R16 is OH, (4) OR, SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO2R20 or —OPOR20R21 when R16 is H, or R15 and R16 taken together are =O; R17 and R18 are independently (1) H, —OH, halogen, ($C_1$-$C_{10}$) alkyl or —($C_1$-$C_{10}$) alkoxy when R6 is H, or halogen, ($C_1$-$C_{10}$) alkyl or —C(O)OR22, (2) H, ($C_1$-$C_{10}$) alkyl amino, (($C_1$-$C_{10}$) alkyl)n amino-($C_1$-$C_{10}$) alkyl, ($C_1$-$C_{10}$) alkoxy, hydroxy-($C_1$-$C_{10}$) alkyl, ($C_1$-$C_{10}$) alkoxy-($C_1$-$C_{10}$) alkyl, (halogen)m ($C_1$-$C_{10}$) alkyl, ($C_1$-$C_{10}$) alkanoyl, formyl, ($C_1$-$C_{10}$) carbalkoxy or ($C_1$-$C_{10}$) alkanoyloxy when R15 and R16 taken together are =O, (3) R17 and R18 taken together are =O; (4) R17 or R18 taken together with the carbon to which they are attached form a 3-6 member ring containing 0 or 1 oxygen atom; or (5) R15 and R17 taken together with the carbons to which they are attached form an epoxide ring; R20 and R21 are independently OH, pharmaceutically acceptable ester or pharmaceutically acceptable ether; R22 is H, (halogen)m ($C_1$-$C_{10}$) alkyl or ($C_1$-$C_{10}$) alkyl; n is 0, 1 or 2; and m is 1, 2 or 3; or pharmaceutically or veterinarily acceptable salts thereof, and/or a ubiquinone of the chemical formula

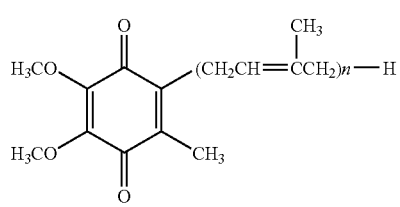

(II)

(CoQ$_n$);

wherein n=1 to 12, the agent being present in an amount effective for treating respiratory lung diseases and conditions, or for reducing levels of, or sensitivity to, adenosine in a subject's tissue(s); or pharmaceutically acceptable salts of either of them.

The above agent is effective for the prevention, prophylaxis and treatment of COPD, and other respiratory and lung diseases and conditions such as bronchoconstriction, lung allergies, asthma, particularly non-steroid responding asthma, inflammation, immune mediated reactions, allergy(ies) and other airway problems, which may be caused by different conditions, including pulmonary vasoconstriction, inflammation, allergies, asthma, impeded respiration, respiratory distress syndrome, pain, cystic fibrosis, allergic rhinitis, pulmonary hypertension, pulmonary vasoconstriction, emphysema, bronchitis, different types of Respiratory Distress Syndrome (RDS), e.g., Acute Respiratory Distress Syndrome (ARDS), cystic fibrosis (CF), and cancers such as leukemias, lymphomas, carcinomas, and the like, e.g. colon cancer, breast cancer, lung cancer, pancreatic cancer, hepatocellular carcinoma, kidney cancer, melanoma, hepatic metastases, etc., as well as all types of cancers which may metastasize or have metastasized to the lung(s), including breast and prostate cancer. The present agents are also suitable for administration before, during and after other treatments, including radiation, chemotherapy, antibody therapy, phototherapy and cancer, and other types of surgery. The present agent is effectively administered prophylactically and therapeutically in conjunction with other therapies, or by itself for conditions without known therapies or as a substitute for therapies that have significant negative side effects. Also provided is a method for reducing or depleting adenosine levels, increasing lung surfactant or ubiquinone levels, or treating hypersensitivity to adenosine, particularly in the lung, liver, heart and/or brain, and treating various respiratory and lung diseases and their symptoms, by administering to a subject in need of such treatment, the active agent(s).

Suitable active agents are non-glucocorticoid steroid, such as an epiandrosterone (EA), e.g., dehydroepiandrosterone (DHEA), or its sulfate derivative (DHEA-S), or analogues thereof, or pharmaceutically acceptable salts thereof, in an amount effective to inhibit or control a variety of respiratory and lung diseases and conditions in the subject. Examples of EAs that may be used to carry out this method are wherein R1, R2, R3, R4, R5, R7, R8, R9, R10, R12, R13, R14 and R19 are independently H, OR, halogen, ($C_1$-$C_{10}$) alkyl or ($C_1$-$C_{10}$) alkoxy, R5 and R11 are independently OH, SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —$OSO_2R20$, —$OPOR20R21$ or ($C_1$-$C_{10}$) alky, R5 and R6 taken together are =O, R10 and R11 taken together are =O; R15 is (1) H, halogen, ($C_1$-$C_{10}$) alkyl, or ($C_1$-$C_{10}$) alkoxy when R16 is —C(O)OR22, (2) H, halogen, OH or ($C_1$-$C_{10}$) alkyl when R16 is halogen, OH or ($C_1$-$C_{10}$) alkyl, (3) H, halogen, ($C_1$-$C_{10}$) alkyl, ($C_1$-$C_{10}$) alkenyl, ($C_1$-$C_{10}$) alkenyl, formyl, ($C_1$-$C_{10}$) alkanoyl or epoxy when R16 is OH, (4) OR, SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —$OSO_2R20$ or —$OPOR20R21$ when R16 is H, or R15 and R16 taken together are =O; R17 and R18 are independently (1) H, —OH, halogen, ($C_1$-$C_{10}$) alkyl or —($C_1$-$C_{10}$) alkoxy when R6 is H, OR, halogen. ($C_1$-$C_{10}$) alkyl or —C(O)OR22, (2) H, (($C_1$-$C_{10}$) alkyl) amino, (($C_1$-$C_{10}$) alkyl)n amino-($C_1$-$C_{10}$) alkyl, ($C_1$-$C_{10}$) alkoxy, hydroxy-($C_1$-$C_{10}$) alkyl, ($C_1$-$C_{10}$) alkoxy-($C_1$-$C_{10}$) alkyl, (halogen)m ($C_1$-$C_{10}$) alkyl, ($C_1$-$C_{10}$) alkanoyl, formyl, ($C_1$-$C_{10}$) carbalkoxy or ($C_1$-$C_{10}$) alkanoyloxy when R15 and R16 taken together are =O, (3) R17 and R18 taken together are =O; (4) R17 or R18 taken together with the carbon to which they are attached form a 3-6 member ring containing 0 or 1 oxygen atom; or (5) R15 and R17 taken together with the carbons to which they are attached form an epoxide ring; R20 and R21 are independently OH, pharmaceutically acceptable ester or pharmaceutically acceptable ether; R22 is H, (halogen)m ($C_1$-$C_{10}$) alkyl or ($C_1$-$C_{10}$) alkyl; n is 0, 1 or 2; and m is 1, 2 or 3; or pharmaceutically or veterinarily acceptable salts thereof.

The hydrogen atom at position 5 of the compound of chemical formula I may be present in the alpha or beta configuration, and the compound may comprise a mixture of both configurations. Compounds illustrative of compounds of chemical formula (I) above include DHEA, wherein R and R1 each comprise hydrogen and the double bond is present; 16-alpha bromoepiandrosterone, where R comprises Br, R1 comprises H, and the double bond is present; 16-alpha-fluoro epiandrosterone, wherein R comprises F, R1 comprises H and the double bond is present; etiocholanolone, where R and R1 each comprise hydrogen and the double bond is absent; and dehydroepiandrosterone sulphate (DHEA-S), wherein R comprises H, R1 comprises SO2OM and M comprises sulphatide as defined above, and the double bond is absent, amongst others. In the compound of formula I, R preferably comprises halogen, e.g. bromo, chloro, or fluoro, R1 comprises hydrogen, and the double bond is present. Most preferably the compound of Formula I comprises 16-α-fluoro epiandrosterone. Compounds of formula (III) or (IV) that are preferred are those where $R^{15}$ and $R^{16}$ together are =O, $R^S$ is —OH or —$OSO_2R^{20}$, or $R^{20}$ is H. Others, however, are also suitable for use with the invention described in this patent.

The compounds of formula I, III and IV may be made in accordance with procedures known in the art, or employing variations thereof that will be apparent to those skilled in the art. See, for example, U.S. Pat. No. 4,956,355, UK Patent No. 2,240,472, EPO Patent Application No. 429,187, Patent Publication WO9104030A1; Abou-Gharbia M. et al., J. Pharm. Sci. 70: 1154-1157 (1981), Merck Index Monograph No. 7710, 11th Ed. (1989).

The active agent may be administered per se or in the form of pharmaceutically acceptable salts, as discussed above. In general, the non-glucocorticvoid steroid, analogues and salts thereof, including DHEA and DHEA-S, are administered in a dosage of about 0.01, about 0.1, about 0.4, about 1, about 5, about 10, about 20 to about 4, about 30, about 70, about 100, about 300, about 1,000, about 3600 mg/kg body weight or in any range thereof. Other dosages, however, are also contemplated. These active compounds may be administered once or several times a day, or any other desirable regime.

The term "ubiquinone", as used herein, refers to a family of compounds having structures based on a w 3-dimethoxy-5-methyl benzoqumone nucleus with a variable terpenoid acid chain containing on to twelve non-unsaturated trans-isoprenoid units. Such compounds are also known in the art as "Coenzyme $Q_n$", wherein n comprises 1 to 12, preferably n comprising 1 to 10, and may be referred to herein as compounds represented by the following chemical formula

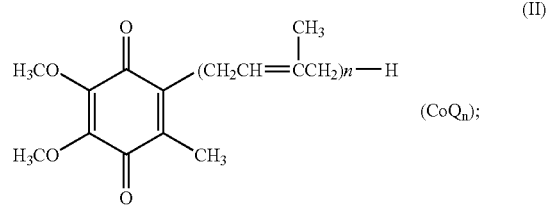

wherein n comprises 1 to 10. In the method of the invention, another preferred ubiquinone is a compound according to the above formula, where n comprises 6 to 10, i.e., Coenzyme $Q_{6-10}$, and most preferably wherein n comprises 10, i.e., Coenzyme $Q_{10}$.

These active agent or compound may be administered per se or in the form of pharmaceutically acceptable salts, either systemically or topically. In general, the ubiquinone is administered in an amount-effective to treat a respiratory, lung or cancer disease or to off-set ubiquinone depletion in the lungs and/or heart, or lung surfactant depletion, if induced by the administration of an EA, that is induced by DHEA, DHEA-S, analog thereof or salt thereof. Accordingly, the dosage of the ubiquinone will vary depending upon the condition of the subject and route of administration. The ubiquinone is preferably administered in a total amount per day of about 1, about 5, about 10, about 15, about 30 to about 50, about 100, about 200, about 300, about 500, about 800, about 1200 mg/kg body weight or in any range thereof, more preferably about 30 to about 600 mg/kg, and most preferably about 50 to about 150 mg/kg. The ubiquinone may be administered in one dose (once) or several times a day.

The ubiquinone may be administered by itself, as a mixture of ubiquinones of varying side chain lengths, or concurrently with the non-glucocorticoid steroid, such as DHEA, DHEA Sulfate (DHEA-S) or other analogues thereof in the preventative, prophylactic and therapeutic methods described above. The phrase "concurrently administering", as used herein, means that the non-glucocorticoid steroid and the ubiquinone are administered either (a) simultaneously in time, preferably by formulating the two together in a common pharmaceutical carrier, or (b) at different times during the course of a common treatment schedule. In the latter case, the non-glucocorticoid steroid and ubiquinone compounds are administered at times sufficiently close so that, in addition to its direct effect, the ubiquinone also offsets ubiquinone depletion in the subject's tissues, e.g. lungs and heart. This timing helps to prevent or counter-balance any deterioration of tissue, e.g. lung and heart, function that may result from the administration of other drugs which include steroids or analogs thereof.

The ubiquinone may be formulated with a pharmaceutically acceptable carrier separately from the non-glucocorticoid steroid, analogue thereof or salt thereof. For example, in some cases the non-glucocorticoid steroid may be administered e.g. into the respiration, or by inhalation, nasally or into the lungs (intrapulmonarily) of the subject whereas the ubiquinone may be administered systemically or otherwise. Nevertheless, the ubiquinone may be formulated by any of the techniques set forth above.

The pharmaceutical composition can further comprise folinic acid, or pharmaceutically acceptable salts thereof. Folinic acid is an intermediate product of the metabolism of folic acid; the active form into which that acid is converted in the body, ascorbic acid being a necessary factor in the conversion process. Folinic acid has been used therapeutically as an antidote to folic acid antagonists such as methotrexate which block the conversion of folic acid into folinic acid. Additionally, folinic acid has been used as an anti-anemic (combating folate deficiency). See *The Merck Index*, Monograph No. 4141 ($11^{th}$ Ed. 1989). Folinic acid and the pharmaceutically acceptable salts thereof (hereafter sometimes referred to as "active compounds") are known, and can be made in accordance with known procedures. See generally The Merck Index, Monograph No. 4141 (11th Ed. 1989); U.S. Pat. No. 2,741,608. Preferably pharmaceutically acceptable salts are alkaline metal or alkaline earth salts, such as sodium, potassium or calcium salts, of the carboxylic acid group of folinic acid. More preferably, the pharmaceutically acceptable salt is the calcium salt of folinic acid.

Other agents that may be incorporated into the present composition are one or more of a variety of therapeutic agents that are administered to humans and animals. Some of the categories of agents suitable for incorporation into the present composition and formulations are analgesics, pre-menstrual medications, agents, anti-aging agents, anti-anxyolytic agents, mood disorder agents, anti-depressants, anti-bipolar mood agents, anti-schyzophrenic agents, anti-cancer agents, alkaloids, blood pressure controlling agents, hormones, anti-inflammatory agents, muscle relaxants, steroids, soporific agents, anti-ischemic agents, anti-arrythmic agents, contraceptives, vitamins, minerals, tranquilizers, neurotransmitter regulating agents, wound healing agents, anti-angyogenic agents, cytokines, growth factors, anti-metastatic agents, antacids, anti-histaminic agents, anti-bacterial agents, anti-viral agents, anti-gas agents, appetite suppressants, sun screens, emolients, skin temperature lowering products, radioactive phosphorescent and fluorescent contrast diagnostic and imaging agents, libido altering agents, bile acids, laxatives, anti-diarrheic agents, skin renewal agents, hair growth agents, analgesics, pre-menstrual medications, anti-menopausal agents such as hormones and the like, anti-aging agents, anti-anxiolytic agents, nociceptic agents, mood disorder agents, anti-depressants, anti-bipolar mood agents, anti-schizophrenic agents, anti-cancer agents, alkaloids, blood pressure controlling agents, hormones, anti-inflammatory agents, other agents suitable for the treatment and prophylaxis of diseases and conditions associated or accompanied with pain and inflammation, such as arthritis, burns, wounds, chronic bronchitis, chronic obstructive pulmonary disease (COPD), inflammatory bowel disease such as Crohn's disease and ulcerative colitis, autoimmune disease such as lupus erythematosus, muscle relaxants, steroids, soporific agents, anti-ischemic agents, anti-arrhythmic agents, contraceptives, vitamins, minerals, tranquilizers, neurotransmitter regulating agents, wound and burn healing agents, anti-angiogenic agents, cytokines, growth factors, anti-metastatic agents, antacids, anti-histaminic agents, anti-bacterial agents, anti-viral agents, anti-gas agents, agents for reperfusion injury, counteracting appetite suppressants, sun screens, emollients, skin temperature lowering products, radioactive phosphorescent and fluorescent contrast diagnostic and imaging agents, libido altering agents, bile acids, laxatives, anti-diarrheic agents, skin renewal agents, hair growth agents, etc.

Among the hormones are female and male sex hormones such as premarin, progesterone, androsterones and their analogues, thyroxine and glucocorticoids, among the libido altering agents are Viagra and other NO-level modulating agents, among the analgesics are over-the-counter medications such as ibuprofen, oruda, aleve and acetaminofen and controlled substances such as morphine and codeine, among the anti-depressants are tricyclics, MAO inhibitors and epinephrine, -γ-amino butyric acid (GABA), dopamine and serotonin level elevating agents, e.g. Prozac, Amytryptilin, Wellbutrin and Zoloft, among the skin renewal agents are Retin-A, hair growth agents such as Rogaine, among the anti-inflammatory agents are non-steroidal anti-inflammatory drugs (NSAIDs) and steroids, among the soporifics are melatonin and sleep inducing agents such as diazepam, cytoprotective, anti-ischemic and head injury agents such as enadoline, and many others. Examples of agents in the different groups are provided in the following list. Examples of analgesics are Acetominophen, Anilerdine, Aspirin, Buprenorphine, Butabital, Butorpphanol, Choline Salicylate, Codeine, Dezocine, Diclofenac, Diflunisal, Dihydrocodeine, Elcatoninin, Etodolac, Fenoprofen, Hydrocodone, Hydromorphone, Ibuprofen, Ketoprofen, Ketorolac, Levorphanol, Magnesium Salicylate, Meclofenamate, Mefenamic Acid, Meperidine, Methadone, Methotrimeprazine, Morphine, Nalbuphine, Naproxen, Opium, Oxycodone, Oxymorphone, Pentazocine, Phenobarbital, Propoxyphene, Salsalate, Sodium Salicylate, Tramadol and Narcotic analgesics in addition to those listed above. See, Mosby's Physician's GenRx. Examples of anti-anxiety agents include Alprazolam, Bromazepam, Buspirone, Chlordiazepoxide, Chlormezanone, Clorazepate, Diazepam, Halazepam, Hydroxyzine, Ketaszolam, Lorazepam, Meprobamate, Oxazepam and Prazepam, among others. Examples of anti-anxiety agents associated with mental depression are Chlordiazepoxide, Amitriptyline, Loxapine Maprotiline and Perphenazine, among others. Examples of anti-inflammatory agents are non-rheumatic Aspirin, Choline Salicylate, Diclofenac, Diflunisal, Etodolac, Fenoprofen, Floctafenine, Flurbiprofen, Ibuprofen, Indomethacin, Ketoprofen, Magnesium Salicylate, Meclofenamate, Mefenamic Acid, Nabumetone, Naproxen, Oxaprozin, Phenylbutazone, Piroxicam, Salsalate, Sodium Salicylate, Sulindac, Tenoxicam, Tiaprofenic Acid, Tolmetin. Examples of anti-inflammatories for ocular treatment are Diclofenac, Flurbiprofen, Indomethacin, Ketorolac, Rimexolone (generally for post-operative treatment). Examples of anti-inflammatories for non-infectious nasal applications are Beclomethaxone, Budesonide, Dexamethasone, Flunisolide, Triamcinolone, and the like. Examples of soporifics (anti-insomnia/sleep inducing agents) such as those utilized for treatment of insomnia, are Alprazolam, Bromazepam, Diazepam, Diphenhydramine, Doxylamine, Estazolam, Flurazepam, Halazepam, Ketazolam, Lorazepam, Nitrazepam, Prazepam Quazepam, Temazepam, Triazolam, Zolpidem and Sopiclone, among others. Examples of sedatives are Diphenhydramine, Hydroxyzine, Methotrimeprazine, Promethazine, Propofol, Melatonin, Trimeprazine, and the like. Examples of sedatives and agents used for treatment of petit mal and tremors, among other conditions, are Amitriptyline HCl, Chlordiazepoxide, Amobarbital, Secobarbital, Aprobarbital, Butabarbital, Ethchiorvynol, Glutethimide, L-Tryptophan, Mephobarbital, MethoHexital Na, Midazolam HCl, Oxazepam, Pentobarbital Na, Phenobarbital, Secobarbital Na, Thiamylal Na, and many others. Agents used in the treatment of head trauma (Brain Injury/Ischemia) include Enadoline HCl (e.g. for treatment of severe head injury, orphan status, Warner Lambert). Examples of cytoprotective agents and agents for the treatment of menopause and menopausal symptoms are Ergotamine, Belladonna Alkaloids and Phenobarbitals. Examples of agents for the treatment of menopausal vasomotor symptoms are Clonidine, Conjugated Estrogens and Medroxyprogesterone, Estradiol, Estradiol Cypionate, Estradiol Valerate, Estrogens, conjugated Estrogens, esterified Estrone, Estropipate and Ethinyl Estradiol. Examples of agents for treatment of symptoms of Pre Menstrual Syndrome (PMS) are Progesterone, Progestin, Gonadotrophic Releasing Hormone, oral contraceptives, Danazol, Luprolide Acetate and Vitamin B6. Examples of agents for the treatment of emotional/psychiatric treatments are Tricyclic Antidepressants including Amitriptyline HCl (Elavil), Amitriptyline HCl, Perphenazine (Triavil) and Doxepin HCl (Sinequan). Examples of tranquilizers, anti-depressants and anti-anxiety agents are Diazepam (Valium), Lorazepam (Ativan), Alprazolam (Xanax), SSRI's (selective Serotonin reuptake inhibitors), Fluoxetine HCl (Prozac), Sertaline HCl (Zoloft), Paroxetine HCl (Paxil), Fluvoxamine Maleate (Luvox), Venlafaxine HCl (Effexor), Serotonin, Serotonin Agonists (Fenfluramine), and other over the counter (OTC) medications. Examples of anti-migraine agents are Imitrex and the like.

The amount of each active agent may be adjusted when, and if, additional agents with overlapping activities are included as discussed in this patent. The dosage of the active compounds, however, may vary depending on age, weight, and condition of the subject. Treatment may be initiated with a small dosage, e.g. less than the optimal dose, of the first active agent of the invention, be it a non-glucocorticoid steroid or a ubiquinone, and optionally other bioactive agents described above. This may be similarly done with the second active agent, until a desirable level is attained. Or vice versa, for example in the case of multivitamins and/or minerals, the subject may be stabilized at a desired level of these products and then administered the first active compound. The dose may be increased until a desired and/or optimal effect under the circumstances is reached. In general, the active agent is preferably administered at a concentration that will afford effective results without causing any unduly harmful or deleterious side effects, and may be administered either as a single unit dose, or if desired in convenient subunits administered at suitable times throughout the day. The second therapeutic or diagnostic agent(s) is (are) administered in amounts which are known in the art to be effective for the intended application. In cases where the second agent has an overlapping activity with the principal agent, the dose of one of the other or of both agents may be adjusted to attain a desirable effect without exceeding a dose range that avoids untoward side effects. Thus, for example, when other analgesic and anti-inflammatory agents are added to the composition, they may be added in amounts known in the art for their intended application or in doses somewhat lower that when administered by themselves.

The active compounds provided in this patent are preferably administered to the subject as a pharmaceutical composition. Pharmaceutical compositions for use in the present invention include formulations suitable for systemic and topical administration, including by inhalation, intrapulmonary infusion, nasal, respirable, oral, topical (including buccal, sublingual, dermal and intraocular), parenteral (including subcutaneous, intradermal, intramuscular, intravenous and intraarticular), and transdermal administration. The compositions may conveniently be provided in bulk, or presented in unit or multiple dosage form, and may be prepared by any of the methods well known in the art.

The active compounds disclosed herein may be administered to the lungs, i.e. intrapulmonarily, nasally, respirably or by inhalation, of a subject by any suitable means. A preferred method of administration is by generating an aerosol or spray comprised of nasal or respirable particles comprising the active compound. The thus administered particles are then inhaled by the subject, i.e. by inhalation, intrapulmonary drip, or nasal administration, or by direct administration into the airways or respiration. The respirable or inhalable particles may be liquid or solid, and they are preferably in the range of about 0.01, 0.05, about 0.5, about 1, about 2, about 2.5, about 3.5, about 4 to about 6, about 8, about 10 micron, and preferably about 1 to about 5 micron (respirable or inhalable particles), or about 8, about 10, about 15, about 20, about 30 to about 50, about 100, about 150, about 200, about 300, about 400, about 500 micron, preferably about 10 to about 50 micron for intrapulmonary instillation or nasal administration. The range of particle size for administering directly to the lungs is about 0.01 μm to about 10 μm. Preferably, it is about 0.05 μm to about 10 μm. The range of particle size for nasal administration is about 10 mm about 100 mm. Preferably, it is about 10 μm to about 50 μm. As explained above, particles of non-respirable size that are included in the aerosol or spray tends to deposit in the throat and be swallowed, and the quantity of non-respirable particles in the aerosol is preferably minimized. For nasal administration or intrapulmonary instillation, particularly for newborn babies and infants, a particle size in the range of about 10 to about 50 microns is preferred to ensure deposition and retention in the nasal or pulmonary cavity.

Liquid pharmaceutical compositions of the active compound for producing an aerosol or spray may be prepared by combining the active compound with a stable vehicle, such as sterile pyrogen free water. Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant that serves to facilitate the formation of an aerosol. A suitable dispersant is lactose, which may be blended with the active compound in any suitable ratio, e.g. a 1 to 1 ratio by weight. Again, other therapeutic and formulation compounds may also be included, such as a surfactant to improve the state of surfactant in the lung and help with the absorption of the active agent.

Aerosols of liquid particles comprising the active agent may be produced by any suitable means, such as with a nebulizer. See, e.g. U.S. Pat. No. 4,501,729. Nebulizers are commercially available devices that transform solutions or suspensions of the active ingredient into a therapeutic aerosol mist either by means of acceleration of a compressed gas, typically air or oxygen, through a narrow venturi orifice or by means of ultrasonic agitation. Suitable compositions for use in nebulizer comprise the active ingredient in a liquid carrier or diluent, the active ingredient comprising about 0.05 up to about 40% w/w of the composition, preferably about 1 to less than about 20% w/w. The carrier is typically water or a dilute aqueous alcoholic solution, preferably made isotonic with body fluids by the addition of, for example sodium chloride. Other carriers, however, are also suitable as an artisan would know. Optional additives include preservatives if the composition is not prepared sterile. Examples of preservatives are methyl hydroxybenzoate, antioxidants, flavoring agents, volatile oils, buffering agents and surfactants. Others, however, are also suitable.

Aerosols of solid particles comprising the active compound may likewise be produced with any solid particulate medicament aerosol generator. Aerosol and spray generators for administering solid particulate medicaments to a subject, comprise product particles that are respirable or inhalable, and they generate a volume of aerosol containing a predetermined metered dose of a medicament at a rate suitable for human administration. Examples of such aerosol and spray generators include metered dose inhalers and insufflators known in the art.

Compositions suitable for oral administration may be presented in discrete units, such as capsules, cachets, lozenges, or tablets, each containing a pre-determined amount of the active compound; as a powder or granules; as a solution or a suspension in an aqueous or non-aqueous liquid; or as an oil-in-water or water-in-oil emulsion. Such compositions may be prepared by any suitable method of pharmacy that includes the step of bringing into association the active compound and a suitable carrier. In general, the compositions of the invention are prepared by uniformly and intimately admixing the active compound with a liquid or finely divided solid carrier, or both, and then, if necessary, shaping the resulting mixture. For example, tablet may be prepared by compressing or molding a powder or granules containing the active compound alone, or optionally with one or more accessory ingredients. Compressed tablets may be prepared by compressing, in a suitable machine, the compound in a free-lowing form, such as a powder or granules optionally mixed with a binder, lubricant, inert diluent, and/or surface active/dispensing agent(s) or surfactants. Molded tablets may be made by molding, in a suitable machine, the powdered compound moistened with an inert liquid binder. Compositions for oral administration may optionally include enteric coatings known in the art to prevent degradation of the compositions in the stomach and provide release of the drug in the small intestine.

Compositions suitable for buccal or sub-lingual administration include lozenges comprising the active compound in a flavored base, usually sucrose and acacia or tragacanth, and pastilles comprising the compound in an inert base such as gelation and glycerin or sucrose and acacia.

Compositions suitable for parenteral administration comprise sterile aqueous and non-aqueous injection solutions, suspensions or emulsions of the active compound, which preparations are preferably isotonic with the blood of the intended recipient. These preparations may contain anti-oxidants, buffers, surfactants, bacteriostats, solutes which render the compositions isotonic with the blood of the intended recipient, and other formulation components known in the art. Aqueous and non-aqueous sterile suspensions may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions, suspensions and emultions may be prepared from sterile powders, granules and tablets of the kind previously described.

Compositions suitable for topical application to the skin preferably take the form of an ointment, cream, lotion, paste, gel, spray, aerosol, or oil, although others are also suitable. Carriers that may be used include vaseline, lanoline, polyethylene glycols, alcohols, transdermal enhancers, and combinations of two or more thereof.

Compositions suitable for rectal and vaginal administration are also included and may be prepared by methods known in the art.

Compositions suitable for transdermal administration may be presented as discrete patches adapted to remain in intimate contact with the epidermis of the recipient for a prolonged period of time. Compositions suitable for transdermal administration may also be delivered by iontophoresis. See, e.g. Pharmaceutical Research 3:318 (1986). They typically take the form of an optionally buffered aqueous solution of the active compound containing appropriate ions to facilitate the iontophoretic delivery of the agent.

The following examples are provided to illustrate the present invention in a more complete manner, and should not be construed as restrictive of the invention.

EXAMPLES

In the examples provided below, EA means an epiandrosterone, DHEA means dehydroepiandrosterone, s means seconds, mg means milligrams, kg means kilograms, kw means kilowatts, Mhz means megahertz, CoQ means a ubiquinone, and nmol means nanomoles.

Examples 1 and 2

In Vivo Effects of Folinic Acid and DHEA on Adenosine Levels

Young adult male Fischer 344 rats (120 grams) were administered dehydroepiandrosterone (DHEA) (300 mg/kg) or methyltestosterone (40 mg/kg) in carboxymethylcellulose by gavage once daily for fourteen days. Folinic acid (50 mg/kg) was administered intraperitoneally once daily for fourteen days. On the fifteenth day, the animals were sacrificed by microwave pulse (1.33 kw, 2450 MHZ, 6.5 s) to the cranium, which instantly denatures all brain protein and prevents further metabolism of adenosine. Hearts were removed from animals and flash frozen in liquid nitrogen with 10 seconds of death. Liver and lungs were removed en bloc and flash frozen within 30 seconds of death. Brain tissue was subsequently dissected. Tissue adenosine was extracted, derivatized to 1, N6-ethenoadenosine and analyzed by high performance liquid chromatography (HPLC) using spectrofluorometric detection according to the method of Clark and Dar (*J. Neuroscience Methods* 25:243 (1988)). Results of these experiments are summarized in Table 1 below. Results are expressed as the mean±SEM, with ψ $p<0.05$ compared to control group and ψ $p<0.05$ compared to DHEA or methyltestosterone-treated groups.

TABLE 1

In Vivo Effect of DHEA, δ-1-methyltestosterone & Folinic Acid on Adenosine Levels in Various Rat Tissues

| | Intracellular Adenosine (nmol/mg protein) Lung | | |
|---|---|---|---|
| | Heart | Lung | Brain |
| Control | 10.6 ± 0.6 (n = 12) | 3.1 ± 0. (n = 6) | 0.5 ± 0.04 (n = 12) |
| DHEA (300 mg/kg) | 6.7 ± 0.5 (n = 12) | 2.3 ± 0.3 (n = 6) | 0.19 ± 0.01 (n = 12) |
| Methyltestosterone (40 mg/kg) | 8.3 ± 1.0 (n = 6) | N.D. | 0.42 ± 0.06 (n = 6) |
| Methyltestost. (M) (120 mg/kg) | 6.0 ± 0.4 (n - 6) | N.D. | 0.32 ± 0.03 (n = 6) |
| Folinic Acid (F.A.) (50 mg/kg) | 12.4 ± 2.1 (n = 5) | N.D. | 0.72 ± 0.09 (n = 5) |
| DHEA+ F.A. (300 mg/kg; 50 mg/kg) | 11.1 ± 0.6 (n = 5) | N.D. | 0.55 ± 0.09 (n = 5) |
| M + F.A. (120 mg/kg; 50 mg/kg) | 9.1 ± 0.4 (n = 6) | N.D. | 0.60 ± 0.06 (n = 6) |

N.D. = Not Determined

The results of these experiments indicate that rats administered DHEA or methyltestosterone daily for two weeks showed multi-organ depletion of adenosine. Depletion was dramatic in brain (60% depletion for DHEA, 34% for high dose methyltestosterone) and heart (37% depletion for DHEA, 22% depletion for high dose Methyltestosterone). Co-administration of folinic acid completely abrogated steroid-mediated adenosine depletion. Folinic acid administered alone induce increase in adenosine levels for all organs studied.

Example 3

Preparation of the Experimental Model

Cell cultures, HT-29 SF cells, which represent a subline of HY-29 cells (ATCC, Rockville, Md.) and are adapted for growth in completely defined serum-free PC-1 medium (Ventrex, Portland, Me.), were obtained. Stock cultures were maintained in this medium at 37° C. in a humidified atmosphere containing 5% $CO_2$. At confluence cultures were replated after dissociation using trypsin/EDTA (Gibco, Grand Island, N.Y.) and re-fed every 24 hours. Under these conditions, the doubling time for HT-29 SF cells during logarithmic growth was 24 hours.

Example 4

Flow Cytometry

Cells were plated at $10^5$/60-mm dish in duplicate. For analysis of cell cycle distribution, cultures were exposed to either 0, 25, 50, or 200 μM DHEA. For analysis of reversal of cell cycle effects of DHEA, cultures were exposed to either 0 or 25 μM DHEA, and the media were supplemented with MVA, CH, RN, MVA plus CH, or MVA plus CH plus RN or were not supplemented. Cultures were trypsinized following 0, 24, 48, or 74 hours and fixed and stained using a modification of a procedure of Bauer et al., *Cancer Res.*, 46:3173-3178 (1986). Briefly, cells were collected by centrifugation and resuspended in cold phosphate-buffered saline. Cells were fixed in 70% ethanol, washed, and resuspended in phosphate-buffered saline. One ml hypotonic stain solution (50 μg/ml propidium iodide (Sigma Chemical Co.), 20 μg/ml Rnase A (Boehringer Mannheim, Indianapolis, Ind.), 30 mg/ml polyethylene glycol, 0.1% Triton X-100 in 5 mM citrate buffer) was then added, and after 10 min at room temperature, 1 ml of isotonic stain solution (propidium iodide, polyethylene glycol, Triton X-100 in 0.4M NaCl) was added and the cells were analyzed using a flow cytometer, equipped with pulse width/pulse area doublet discrimination (Becton Dickinson Immunocytometry Systems, San Jose, Calif.) After calibration with fluorescent beads, a minimum of $2 \times 10^4$ cells/sample were analyzed, data were displayed s total number of cells in each of 1024 channels of increasing fluorescence intensity, and the resulting histogram was analyzed using the Cellfit analysis program (Becton Dickinson).

Example 5

DHEA Effect on Cell Growth

Cells were plated 25,000 cells/30 mm dish in quadruplicate, and after 2 days received 0, 12.5, 25, 50, or 200 μM DHEA. Cell number was determined 0, 24, 48, and 72 hours later using a Coulter counter (model Z, Coulter Electronics, Inc., Hialeah, Fla.). DHEA (AKZO, Basel, Switzerland) was dissolved in dimethyl sulfoxide, filter sterilized, and stored at −20° C. until use.

FIG. 1 illustrates the inhibition of growth for HT-29 cells by DHEA. Points refer to numbers of cells, and bars refer to SEM. Each data point was performed in quadruplicate, and the experiment was repeated three times. Where SEM bars are not apparent, SEM was smaller than symbol. Exposure to DHEA resulted in a reduced cell number compared to controls after 72 hours in 12.5 UM, 48 hours in 25 or 50 μM, and 24 hours in 200 μM DHEA, indicating that DHEA produced a time- and dose-dependent inhibition of growth.

Example 6

DHEA Effect on Cell Cycle

Figure 2B:
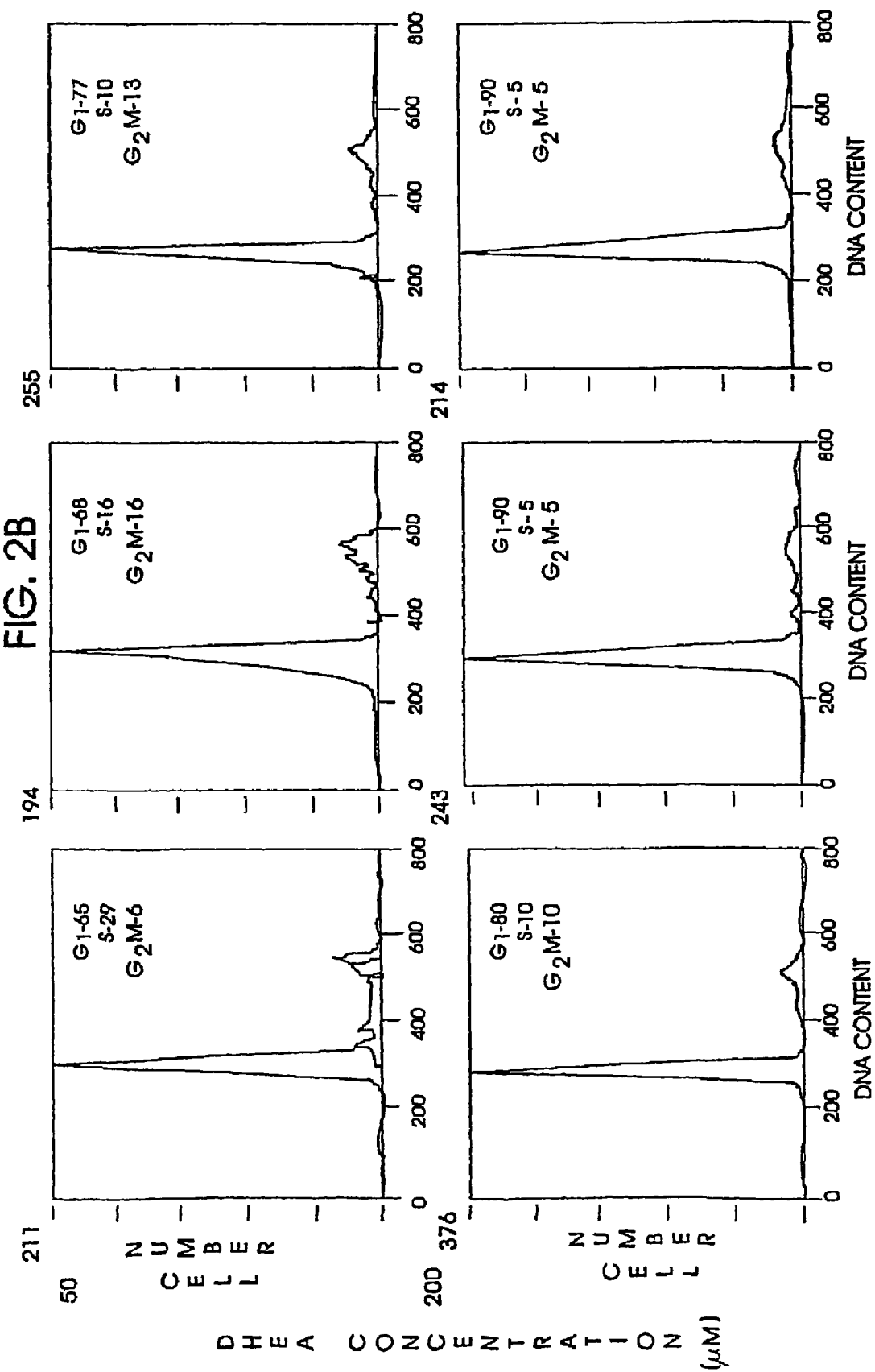
Figure 4C:
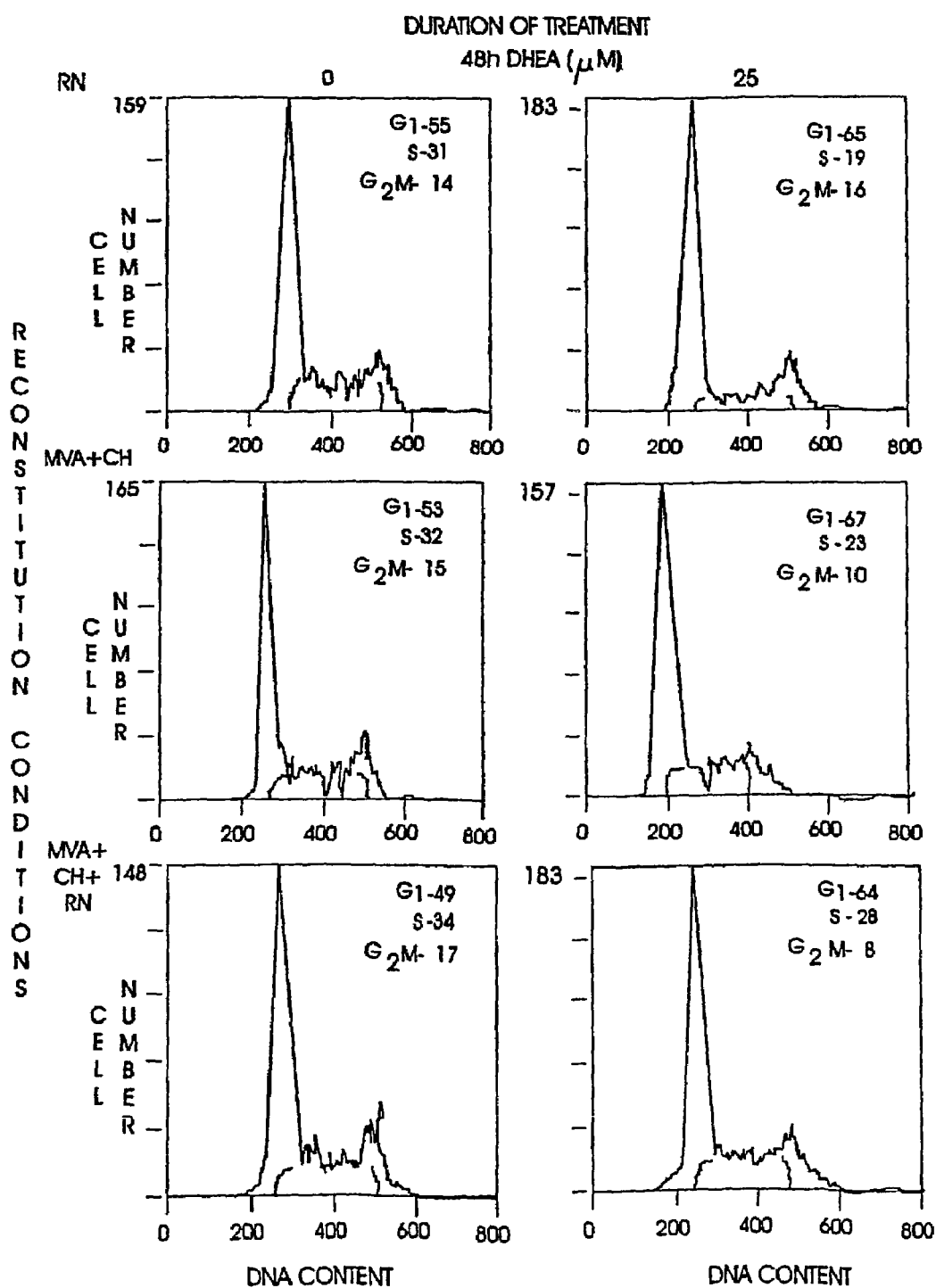

To examine the effects of DHEA on cell cycle distribution, HT-29 SF cells were plated ($10^5$ cells/60 mm dish), and 48 hours later treated with 0.25, 50, or 200 μM DHEA. FIGS. 2A and 2B illustrate the effects of DHEA on cell cycle distribution in HT-29 SF cells. After 24, 48, and 72 hours, cells were harvested, fixed in ethanol, and stained with propidium iodide, and the DNA content/cell was determined by flow cytometric analysis. The percentage of cells in $G_1$, S, and $G_2M$ phases was calculated using the Cellfit cell cycle analysis program. S phase is marked by a quadrangle for clarity. Representative histograms from duplicate determinations are shown. The experiment was repeated three times.

The cell cycle distribution in cultures treated with 25 or 50 μM DHEA was unchanged after the initial 24 hours. However, as the time of exposure to DHEA increased, the proportion of cells in S phase progressively decreased, and the percentage of cells in $G_1$, S and $G_2M$ phases was calculated using the Cellfit cell cycle analysis program. S phase is marked by a quadrangle for clarity. Representative histograms from duplicate determinations are shown. The experiment was repeated three times.

The cell cycle distribution in cultures treated with 25 or 50 μM DHEA was unchanged after the initial 24 hours. However, as the time of exposure to DHEA increased, the proportion of cells in S phase progressively decreased and the percentage of cells in $G_1$ phase was increased after 72 hours. A transient increase in $G_2M$ phase cells was apparent after 48 hours. Exposure to 200 μM DHEA produced a similar but more rapid increase in the percentage of cells in $G_1$ and a decreased proportion of cells in S phase after 24 hours, which continued through the treatment. This indicates that DHEA produced a $G_1$ block in HT-29 SF cells in a time-and dose-dependent manner.

Example 7

Reversal of DHEA-mediated Effect on Growth & Cell Cycle

Cells were plated as above, and after 2 days received either 0 or 25 μM DHEA-containing medium supplemented with mevalonic acid ("MVA"; μM) squalene ("SQ"; 80 μM), cholesterol ("CH"; 15 μg/ml), MVA plus CH, ribonucleosides ("RN"; uridine, cytidine, adenosine, and guanosine at final concentrations of 30 μM each), deoxyribonucleosides ("DN"; thymidine, deoxycytidine, deoxyadenosine and deoxyguanosine at final concentrations of 20 μM each). RN plus DN, or MVA plus CH plus RN, or medium that was not supplemented. All compounds were obtained from Sigma Chemical Co. (St. Louis, Mo.) Cholesterol was solubilized in ethanol immediately before use. RN and DN were used in maximal concentrations shown to have no effects on growth in the absence of DHEA.

FIGS. 3A and 3B illustrate the reversal of DHEA-induced growth inhibition in HT-29 SF cells. In A, the medium was supplemented with 2 μM MVA, 80 μM SQ, 15 μg/ml CH, or MVA plus CH (MVA+CH) or was not supplemented (CON). In B, the medium was supplemented with a mixture of RN containing uridine, cytidine, adenosine, and guanosine in final concentrations of 30 μM each; a mixture of DN containing thymidine, deoxycytidine, deoxyadenosine and deoxyguanosine in final concentrations of 20 μM each; RN plus DN (RN+DN); or MVA plus CH plus RN (MVA+CH+RN). Cell numbers were assessed before and after 48 hours of treatment, and culture growth was calculated as the increase in cell number during the 48 hour treatment period. Columns represent cell growth percentage of untreated controls; bars represent SEM. Increase in cell number in untreated controls was 173,370"6518. Each data point represents quadruplicate dishes from four independent experiments. Statistical analysis was performed using Student's t test ψ $p<0.01$; κ p, 0.001; compared to treated controls. Note that supplements had little effect on culture growth in absence of DHEA.

Under these conditions, the DHEA-induced growth inhibition was partially overcome by addition of MVA as well as by addition of MVA plus CH. Addition of SQ or CH alone had no such effect. This suggest that the cytostatic activity of DHEA was in part mediated by depletion of endogenous mevalonate and subsequent inhibition of the biosynthesis of an early intermediate in the cholesterol pathway that is essential for cell growth. Furthermore, partial reconstitution of growth was found after addition of RN as well as after addition of RN plus DN but not after addition of DN, indicating that depletion of both mevalonate and nucleotide pools is involved in the growth-inhibitory action of DHEA. However, none of the reconstitution conditions including the combined addition of MVA, CH, and RN completely overcame the inhibitory action of DHEA, suggesting either cytotoxic effects or possibly that additional biochemical pathways are involved.

Example 8

Reversal of DHEA Effect on Cell Cycle

HT-29 SF cells were treated with 25 FM DHEA in combination with a number of compounds, including MVA, CH, or RN, to test their ability to prevent the cell cycle-specific effects of DHEA. Cell cycle distribution was determined after 48 and 72 hours using flow cytometry.

FIGS. 4A to 4D illustrate reversal of DHEA-induced arrest in HT-29 SF cells. Cells were plated ($10^5$ cells/60 mm dish) and 48 hours later treated with either 0 or 25 FM DHEA. The medium was supplemented with 2 FM MVA; 15 Fg/ml CH; a mixture of RN containing uridine, cytidine, adenosine, and guanosine in final concentrations of 30 FM; MVA plus CH (MVA+CH); or MVA plus CH plus RN (MVA+CH+RN) or was not supplemented. Cells were harvested after 48 or 72 hours, fixed in ethanol, and stained with propidium iodine, and the DNA content per cell was determined by flow cytometric analysis. The percentage of cells in $G_1$, S, and $G_2M$ phases were calculated using the Cellfit cell cycle profile analysis program. S phase is marked by a quadrangle for clarity. Representative histograms from duplicative determinations are shown. The experiment was repeated two times. Note that supplements had little effect on cell cycle progression in the absence of DHEA.

With increasing exposure time, DHEA progressively reduced the proportion of cells in S phase. While inclusion of MVA partially prevented this effect in the initial 48 hours but not after 72 hours, the addition of MVA plus CH was also able to partially prevent S phase depletion at 72 hours, suggesting a requirement of both MVA and CH for cell progression during prolonged exposure. The addition of MVA, CH, and RN was apparently most effective at reconstitution but still did not restore the percentage of S phase cells to the value seen in untreated control cultures. CH or RN alone had very little effect at 48 hours and no effect at 72 hours.

Morphologically, cells responded to DHEA by acquiring a rounded shape, which was prevented only by the addition of MVA to the culture medium (data not shown). Some of the DNA histograms after 72 hours DHEA exposure in FIG. 4 also show the presence of a subpopulation of cells possessing apparently reduced DNA content. Since the HT-29 cell line is known to carry populations of cells containing varying numbers of chromosomes (68-72; ATCC), this may represent a subset of cells that have segregated carrying fewer chromosomes.

Example 9

Conclusions

The examples above provide evidence that in vitro exposure of HT-29 SF human colonic adenocarcinoma cells to concentrations of DHEA known to deplete endogenous mevalonate results in growth inhibition and $G_1$ arrest and that addition of MVA to the culture medium in part prevents these effects. DHEA produced effects upon protein isoprenylation which were in many respects similar to those observed for specific 3-hydroxy-3-methyl-glutaryl-CoA reductase inhibitors such as lovastatin and compactin. Unlike direct inhibitors of mevalonate biosynthesis, however, DHEA mediates its effects upon cell cycle progression and cell growth in a pleiotropic manner involving ribo-and deoxyribonucleotide biosynthesis and possibly other factors as well.

Example 10

Effect of CoQs & an EA on In Vitro NADPH Levels

Glucose-6-Phosphate Dehydrogenase (G6PD) is an important enzyme that is widespread in mammals, and is involved in the conversion of NADP to NADPH, thereby increasing NADPH levels. An inhibition of the G6PD enzyme, thus, will be expected to result in a reduction of cellular NADPH levels, which event, in turn, will be expected to inhibit pathways that are heavily dependent on NADPH. One such pathway, the so-called One-Carbon-Pool pathway, also known as the Folate Pathway, is directly involved in the production of adenosine by addition of the $C_2$ and $C_8$ carbon atoms of the purine ring. Consequently, the inhibition of this pathway will lead to adenosine depletion.

The present invention is broadly applicable to Epiandrosterones (EAs) and Ubiquinones (CoQs). The description of the pathways involved in the present invention are described in the Background section. The present experiment was designed to show that one EA and two CoQs inhibit NADPH levels. DHEA, an Epiandrosterone, has already been shown to decrease levels of adenosine in various tissues. See, Examples 1 and 2 above. The fact that two CoQs are shown to lower NADPH levels to a similar extent as an Epiandrosterone, let alone to a similar extent ensures that the NADPH reduction caused by the CoQs will also result in lower cellular adenosine levels or in adenosine cell depletion. Thus, in accordance with the invention, both Epiandrosterones and Ubiquinones decrease levels of adenosine and, therefore, are useful as medicaments for use in the treatment of diseases where a decrease of adenosine levels or its depletion is desirable, including respiratory diseases such as asthma, bronchoconstriction, lung inflammation and allergies and the like. Both Ubiquinones and DHEA inhibit NADPH levels in a statistically significant manner, when compared to a control. Moreover, the Ubiquinone inhibits NADPH levels to a similar extent as DHEA. The present invention is broadly applicable to the use of Epiandrosterones (EAs) and Ubiquinones (CoQs) to the treatment of respiratory and lung diseases, and other diseases associated with varying levels of adenosine, adenosine hypersensitivity, asthma, bronchoconstriction, and/or lung inflammation and allergies. The DHEA and Ubiquinones employed in the present experiments are equivalent to those described and exemplified above.

Enzymatic Assay of Purified G6PDH

The reaction mixture contained 50 mM glycyl glycine buffer, pH 7.4, 2 mM D-glucose-6-phosphate, 0.67 mM Beta-NADP, 10 mM $MgCl_2$ and 0.0125 units of G6PDH in a final volume of 3.0 ml. All experiments were repeated 4 times.

The control group contained 3 samples that were added no DHEA or Ubiquinone. The experimental group contained a similar number of samples (3) for each concentration of DHEA or Ubiquinone. One group was added DHEA (in triplicate) at different concentrations. A second group was added different concentrations of a CoQ of long side chain (in triplicate), and a third group received a CoQ of short side chain (in triplicate), both at various doses in the μM range.

The reaction was started by addition of the enzyme, and the increase in absorbance at 340 run was measured for 5 minutes. Each data point was conducted in triplicate, and the fall experiment was repeated 4 times.

Both DHEA and the Ubiquinones inhibited the enzyme activity in a statistically significant manner when compared to controls. DHEA was found to inhibit by 72% in vitro the activity of purified G6PDH when compared to control. Both Ubiquinones inhibited the activity of purified G6PDH in vitro by an amount that was not statistically significantly different from that of DHEA. Both DHEA and the Ubiquinones inhibited the enzyme in a statistically significant manner when compared to controls. Both long chain and short chain CoQs were found to be effective inhibitors of G6PDH.

The above results clearly indicate that CoQ reduced cellular levels of NADPH to an extent similar to DHEA and consequently cellular adenosine leves, and has a therapeutic effect on diseases and conditions associated with them. The present results hsow that CoQs have a therapeutic effect similar to that of epiandrosterones. The pathways involved in the present invention, as descripted above, show the criticality of the results reported here, showing that an Epiandrosterone (DHEA) and show Ubiquinones inhibit NADPH levels in a statistically significant manner. The same epiandrosterone (DHEA) was shown in Examples 1 and 2 to decrease levels of adenosine in various tissues. The two different Ubiquinones emplyed lowered NADPH levels to a similar extent as DHEA. The NADPH reduction caused by the Ubiquinones will, in the case of DHEA, result in lower cellular adenosine levels or adenosine depletion. Thus, in accordance with the invention, both Epiandrosterones and Ubiquinones decrease levels of adenosine and are, therefore, useful in the therapy of diseases and conditions where a decrease of adenosine levels or its depletion are desirable, including respiratory and airway diseases such as asthma, bronchoconstriction, lung inflammation and allergies, and the like.

These are clearly superior results, which could not have been expected based on the knowledge of the art at the time of this invention. The experimental data and results provided are clearly enabling of the effect of Ubiquinones on adenosine cellular levels and, therefore, on its therapeutic affect on diseases and conditions associated with them, as described and claimed in this patent.

In Examples 11 to 16 micronized DHEA and micronized Ubiquinone are added in the proportions given below either dry or after predispersal in a small quantity of stabilizer, disodium dioctylsulphosuccinate, lecithin, oleic acid or sorbitan trioleate/trichloro-fluoromethane solution to a suspension vessel containing the main bulk of the trichlorofluoromethane solution. The resulting suspension is further dispersed by an appropriate mixing system using, for example, a high shear blender, ultrasonics or a microfluidiser until an ultrafine dispersion is created. The suspension is then continuously recirculated to suitable filling equipment designed for cold fill or pressure filling of dichlorodifluoromethane. The suspension may be also prepared in a suitable chilled solution of stabilizer, in trichlorofluoromethane/dichlorodifluoromethane.

| Metered Dose Inhaler | |
|---|---|
| Active Ingredient | Target per Actuation |
| Example 11: | |
| Ubiquinone | 200 mg |
| DHEA | 200 mg |
| Stabilizer | 5.0 μg |
| Trichlorofluoromethane | 23.70 mg |
| Dichlorodifluoromethane | 61.25 mg |

-continued

Metered Dose Inhaler

| Active Ingredient | Target per Actuation |
|---|---|
| Example 12: | |
| Ubiquinone | 200 mg |
| DHEA-S | 200 mg |
| Stabilizer | 7.5 µg |
| Trichlorofluoromethane | 23.67 mg |
| Dichlorodifluoromethane | 61.25 mg |
| Example 13: | |
| DHEA | 300 mg |
| Ubiquinone | 300 mg |
| Stabilizer | 25.0 µg |
| Trichlorofluoromethane | 23.45 mg |
| Dichlorodifluoromethane | 61.25 mg |
| Example 14: | |
| Ubiquinone | 300 mg |
| DHEA-S | 300 mg |
| Stabilizer | 15.0 µg |
| Trichlorofluoromethane | 23.56 mg |
| Dichlorodifluoromethane | 61.25 mg |
| Example 15: | |
| Ubiquinone | 100 mg |
| DHEA-S | 100 mg |
| Stabilizer | 15.0 µg |
| Trichlorofluoromethane | 23.56 mg |
| Dichlorodifluoromethane | 61.25 mg |
| Example 16: | |
| DHEA | 100 mg |
| Ubiquinone (CoQ$_{10}$) | 100 mg |
| Stabilizer | 25.0 µg |
| Trichlorofluoromethane | 23.43 mg |
| Dichlorodifluoromethane | 61.25 mg |

In the following Examples 17 to 22, the active ingredients are micronized and bulk blended with lactose in the proportions given above. The blend is filled into hard gelatin capsules or cartridges or into specifically constructed double foil blister packs (Rotadisks blister packs, Glaxo®) to be administered by an inhaler such as the Rotahaler inhaler (Glaxo®) or in the case of the blister packs with the Diskhaler inhaler (Glaxo®).

Metered Dose Dry Powder Formulation

| Active Ingredient | | /cartridge or blister |
|---|---|---|
| Example 17: | | |
| Salmeterol (hydroxynaphthoate) | | 72.5 µg |
| DHEA | | 1 mg |
| Lactose Ph. Eur. | To | 12.5 or 25.0 mg |
| Example 18: | | |
| Ubiquinone | | 0.5 µg |
| DHEA | | 1 mg |
| Lactose Ph. Eur. | To | 12.5 or 25.0 mg |
| Example 19: | | |
| DHEA-S | | 0.5 µg |
| Ubiquinone (CoQ$_{10}$) | | 1 mg |
| Lactose Ph. Eur. | To | 12.5 or 25.0 mg |
| Example 20: | | |
| Ubiquinone | | 0.5 µg |
| DHEA | | 0.5 mg |
| Lactose Ph. Eur. | to | 12.5 or 25.0 mg |

-continued

Metered Dose Dry Powder Formulation

| Active Ingredient | | /cartridge or blister |
|---|---|---|
| Example 21: | | |
| DHEA | | 0.5 µg |
| DHEA-S | | 0.5 mg |
| Lactose Ph. Eur. | to | 12.5 or 25.0 mg |
| Example 22: | | |
| DHEA | | 0.75 µg |
| DHEA-S | | 0.75 mg |
| Lactose Ph. Eur. | To | 12.5 or 25.0 mg |

The foregoing examples are illustrative of the present invention, and are not to be construed as limiting thereof. The invention is defined by the following claims, with equivalents of the claims to be included therein.

Although the invention has been described with reference to the presently preferred embodiments, it should be understood that various modifications can be made without departing from the spirit of the invention.

All publications, patents, and patent applications, and web sites are herein incorporated by reference in their entirety to the same extent as if each individual publication, patent, or patent application, was specifically and individually indicated to be incorporated by reference in its entirety.

What is claimed is:

1. A method for treating chronic obstructive pulmonary disease comprising administering to a subject need of such treatment a pharmaceutical composition comprising a pharmaceutically acceptable carrier or diluent and a therapeutically effective amount of an active agent selected from a non-glucocorticoid steroid having the chemical formula

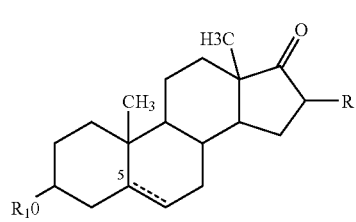

(I)

wherein the broken line represents a single or a double bond; R is hydrogen or a halogen; the H at position 5 is present in the alpha or beta configuration or the compound of chemical formula I comprises a racemic mixture of both configurations;

and R$^1$ is hydrogen or SO$_2$OM, wherein M is selected from the group consisting of H, Na, sulfatide

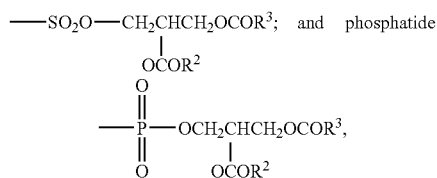

wherein R$^2$ and R$^3$, which may be the same or different, are straight or branched (C$_1$-C$_{14}$) alkyl or glucuronide

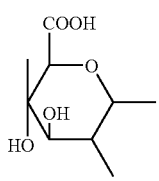

or a non-glucocorticoid steroid of the chemical formula

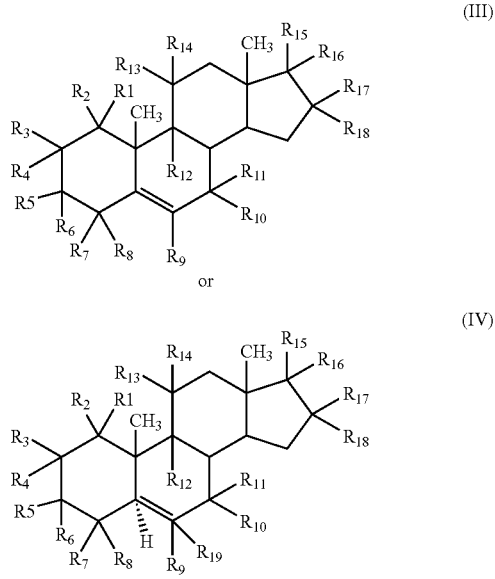

wherein R1, R2, R3, R4, R5, R7, R8, R9, R10, R12, R13, R14 and R19 are independently H, OR, halogen, $(C_1-C_{10})$ alkyl or $(C_1-C_{10})$ alkoxy, R5 and R11 are independently OH, SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaccharide, spirooxirane, spirothirane, —OSO2R20, —OPOR20R21 or $(C_1-C_{10})$ alky, R5 and R6 taken together are =O, R10 and R11 taken together are =O; R15 is (1) H, halogen, $(C_1-C_{10})$ alkyl, or $(C_1-C_{10})$ alkoxy when R16 is —C(O)OR22, (2) H, halogen, OH or $(C_1-C_{10})$ alkyl when R16 is halogen, OH or $(C_1-C_{10})$ alkyl, (3) H, halogen, $(C_1-C_{10})$ alkyl, $(C_1-C_{10})$ alkenyl, $(C_1-C_{10})$ alkynyl, formyl, $(C_1-C_{10})$ alkanoyl or epoxy when R16 is OH, (4) OR, SH, H, halogen, pharmaceutically acceptable ester, pharmaceutically acceptable thioester, pharmaceutically acceptable ether, pharmaceutically acceptable thioether, pharmaceutically acceptable inorganic esters, pharmaceutically acceptable monosaccharide, disaccharide or oligosaceharide, spirooxirane, spirothirane, —OSO2R20 or —OPOR20R21 when R16 is H, or R15 and R16 taken together are =O; R17 and R18 are independently (1) H, —OH, halogen, $(C_1-C_{10})$ alkyl or —$(C_1-C_{10})$ alkoxy when R6 is H, OR, halogen, $(C_1-C_{10})$ alkyl or —C(O)OR22, (2) H, $(C_1-C_{10})$alkylamino, $((C_1-C_{10})$ alkyl)n amino-$(C_1-C_{10})$ alkyl, $(C_1-C_{10})$ alkoxy, hydroxy $(C_1-C_{10})$ alkyl, $(C_1-C_{10})$ alkoxy —$(C_1-C_{10})$ alkyl, (halogen)m $(C_1-C_{10})$ alkyl, $(C_1-C_{10})$ alkanoyl, formyl, $(C_1-C_{10})$ carbalkoxy or $(C_1-C_{10})$ alkanoyloxy when R15 and R16 taken together are =O, (3) R17 and R18 taken together are =O; (4) R17 or R18 taken together with the carbon to which they are attached form a 3-6 member ring containing 0 or 1 oxygen atom; or (5) R15 and R17 taken together with the carbons to which they are attached form an epoxide ring; R20 and R21 are independently OH, pharmaceutically acceptable ester or pharmaceutically acceptable ether; R22 is H, (halogen)m $(C_1-C_{10})$ alkyl or $(C_1-C_{10})$ alkyl; n is 0, 1 or 2; and m is 1, 2 or 3; or pharmaceutically or veterinarily acceptable salts thereof.

2. The method of claim 1, wherein said pharmaceutical composition is of respirable or inhalable particle size.

3. The method of claim 2, wherein said particle size is about 0.1 μm to 500 μm in size.

4. The method of claim 3, wherein said particle size is about 0.1 μm to 10 μm in size.

5. The method of claim 4, wherein said particle size is about 0.5 μm to 10 μm in size.

6. The method of claim 3, wherein said particle size is about 10 μm to 500 μm in size.

7. The method of claim 1, wherein said pharmaceutical composition is an aerosol or spray.

8. The method of claim 1, wherein said active agent is in an amount effective for reducing or depleting levels of, or reducing sensitivity to, adenosine, producing bronchodilation, or increasing levels of ubiquinone or lung surfactant, or treating bronchoconstriction, lung inflammation or allergies or a respiratory, lung or malignant disease or condition.

9. The method of claim 1, comprising about 0.05 to about 40% w/w of said active agent.

10. The method of claim 1, comprising about 1 to about 20% w/w of said active agent.

11. The method of claim 1, wherein said active agent is dehydroepiandrosterone or dehydroepiandrosterone-sulfate.

12. The method of claim 1, wherein said active agent is a compound of formula (I), wherein R is Br, $R^1$ is H, and the broken line represents a double bond, or 16-alpha bromoepiandrosterone.

13. The method of claim 1, wherein said active agent is a compound of formula (I), wherein R is F, $R^1$ is H and the broken line represents a double bond, or 16-alpha-fluoro epiandrosterone.

14. The method of claim 1, wherein said active agent is a compound of formula (I), wherein R and $R^1$ are each hydrogen and the broken line represents a double bond, or etiocholanolone.

15. The method of claim 1, wherein the compound of formula (I), wherein R is H, $R^1$ is $SO_2OM$ and M is a sulfatide group as defined above, and the broken line represents a single bond, or dehydroepiandrosterone sulfate.

16. The method of claim 1, wherein in the compound of formula (I), R is halogen selected from Br, Cl or F, $R^1$ is H, and the broken line represents a double bond.

17. The method of claim 1, wherein the compound of formula (I) is 16-alpha-fluoro epiandrosterone.

18. The method of claim 1, wherein the compound of formula (III) or (IV), is selected from those wherein R15 and R16 together are =O, R5 is —OH, or —OSO2R20, or R is H, and pharmaceutically or veterinarily acceptable salts thereof.

19. The method of claim 1, wherein the compound of formula (I) is 16-alpha-bromo epiandrosterone.

20. The method of claim 1, wherein said pharmaceutical composition is a systemic or topical formulation.

21. The method of claim 20, wherein said systemic or topical formulation is in the form of a formulation selected from buccal, sublingual, dermal, intraocular, vaginal, rectal, intraarticular, intrapulmonary, respirable, oral, inhalable, nasal, topical, parenteral, or transdermal formulation.

22. The method of claim 21, wherein said oral formulation is one selected from capsules, cachets, lozenges, tablets, powder, granules, solutions, suspensions and emulsions.

23. The method of claim 1, wherein the pharmaceutical composition further comprises folinic acid.

24. The method of claim 1, wherein said active agent is dehydroepiandrosterone-sulfate.

* * * * *